United States Patent
Cho et al.

(10) Patent No.: US 9,981,135 B2
(45) Date of Patent: May 29, 2018

(54) MULTI-CHAMBER INTRACARDIAC PACING SYSTEM

(71) Applicant: Medtronic, Inc., Minneapolis, MN (US)

(72) Inventors: Yong K Cho, Excelsior, MN (US); Wade M Demmer, Coon Rapids, MN (US); Michael D Eggen, Chisago City, MN (US); Kathryn Hilpisch, Cottage Grove, MN (US); Michael F Hess, Minneapolis, MN (US); Todd J Sheldon, North Oaks, MN (US); Saul E Greenhut, Aurora, CO (US)

(73) Assignee: Medtronic, Inc., Minneapolis, MN (US)

( * ) Notice: Subject to any disclaimer, the term of this patent is extended or adjusted under 35 U.S.C. 154(b) by 394 days.

(21) Appl. No.: 14/645,038

(22) Filed: Mar. 11, 2015

(65) Prior Publication Data
US 2016/0015985 A1    Jan. 21, 2016

Related U.S. Application Data

(60) Provisional application No. 62/025,716, filed on Jul. 17, 2014.

(51) Int. Cl.
| | |
|---|---|
| *A61N 1/37* | (2006.01) |
| *A61N 1/365* | (2006.01) |
| *A61N 1/362* | (2006.01) |
| *A61N 1/375* | (2006.01) |
| *A61N 1/36* | (2006.01) |
| *A61B 5/00* | (2006.01) |
| *A61B 5/0464* | (2006.01) |

(Continued)

(52) U.S. Cl.
CPC ......... *A61N 1/3706* (2013.01); *A61B 5/0464* (2013.01); *A61B 5/686* (2013.01); *A61N 1/36* (2013.01); *A61N 1/3622* (2013.01); *A61N 1/36592* (2013.01); *A61N 1/3756* (2013.01); *A61B 5/0402* (2013.01); *A61N 1/37205* (2013.01)

(58) Field of Classification Search
CPC .... A61N 1/37288; A61N 1/3756; A61N 1/37; A61N 1/362; A61N 1/365; A61N 1/3706; A61N 1/36592; A61N 1/3622; A61N 1/36; A61B 5/686; A61B 5/0464
USPC .......................................................... 607/4
See application file for complete search history.

(56) References Cited

U.S. PATENT DOCUMENTS

| | | |
|---|---|---|
| 5,113,859 A | 5/1992 | Funke |
| 5,507,782 A | 5/1996 | Kieval |
| 5,683,432 A | 11/1997 | Goedeke |

(Continued)

OTHER PUBLICATIONS (PCT/US2015/040298) PCT Notification of Transmittal of the International Search Report and the Written Opinion of the International Searching Authority, dated Sep. 228, 2015, 10 pages.

*Primary Examiner* — Carl H Layno
*Assistant Examiner* — Jon Eric C Morales

(57) ABSTRACT

A medical device system including at least a first implantable medical device and a second implantable medical device is configured to establish by a control module of the first implantable medical device whether the second implantable medical device is present in a patient and self-configure an operating mode of the control module in response to establishing that the second implantable medical device is present.

23 Claims, 9 Drawing Sheets

(51) Int. Cl.
  *A61N 1/372* (2006.01)
  *A61B 5/0402* (2006.01)

(56) References Cited

U.S. PATENT DOCUMENTS

| | | |
|---|---|---|
| 6,477,415 B1 | 11/2002 | Yerich |
| 6,772,005 B2 | 8/2004 | Casavant |
| 7,031,772 B2 | 4/2006 | Condie |
| 7,149,577 B2 | 12/2006 | Sharma |
| 7,218,965 B2 | 5/2007 | Casavant |
| 7,248,924 B2 | 7/2007 | Casavant |
| 7,515,960 B2 | 4/2009 | Sharma |
| 7,623,911 B2 | 11/2009 | Sarkar |
| 7,689,279 B2 | 3/2010 | Ziegler |
| 7,742,812 B2 | 6/2010 | Ghanem |
| 7,869,876 B2 | 1/2011 | Prakash |
| 8,170,666 B2 | 5/2012 | Sheldon |
| 8,401,629 B2 | 3/2013 | Stadler |
| 8,433,409 B2 | 4/2013 | Johnson |
| 8,532,785 B1 | 9/2013 | Crutchfield |
| 8,541,131 B2 | 9/2013 | Lund |
| 8,744,572 B1 | 6/2014 | Greenhut et al. |
| 8,798,745 B2 | 8/2014 | Jacobson |
| 2008/0086185 A1* | 4/2008 | Amurthur .......... A61N 1/36114 607/60 |
| 2008/0114408 A1 | 5/2008 | Shuros et al. |
| 2012/0172892 A1 | 7/2012 | Grubac |
| 2013/0035748 A1 | 2/2013 | Bonner |
| 2014/0100633 A1 | 4/2014 | Mann et al. |
| 2014/0121720 A1 | 5/2014 | Bonner et al. |

* cited by examiner

MULTI-CHAMBER INTRACARDIAC PACING SYSTEM

CROSS-REFERENCE TO RELATED APPLICATIONS

The present application claims priority to U.S. Provisional Patent Application No. 62/025,716, which was filed Jul. 17, 2014, and is hereby incorporated herein by reference in its entirety.

TECHNICAL FIELD

The disclosure relates to an implantable medical device system and associated method for controlling the monitoring and therapy delivery functions of an intracardiac pacing device.

BACKGROUND

Implantable cardiac pacemakers are commonly placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one medical lead for positioning electrodes in one heart chamber, atrial or ventricular, or a dual chamber pacemaker coupled to two leads for positioning electrodes in both an atrial and a ventricular chamber. Multi-chamber pacemakers are also available that may be coupled to three leads for positioning electrodes for pacing and sensing in one atrial chamber and both the right and left ventricles.

The pacing mode of a pacemaker is commonly designated by a three- or four-letter code. The first letter may be an "A" for atrial, "V" for ventricular or "D" for dual (atrial and ventricular) to indicate which chamber(s) are paced. The second letter indicates which chamber(s) are sensed again designated by an "A," "V," or "D." The third letter indicates how the pacemaker responds when it senses a cardiac event. For example, a sensed cardiac event may trigger a pacing pulse and is indicated by a letter "T" or a sensed cardiac event may inhibit a pacing pulse and is indicated by a letter "I." In some cases, sensed cardiac events may both trigger and inhibit a pacing pulse depending on which chamber the event was sensed in. This dual response is indicated by the third letter "D."

By this convention, an AAI pacing mode delivers pacing pulses in an atrial chamber, senses atrial P-waves attendant to atrial depolarization in the atrium, and inhibits the atrial pacing pulse when a P-wave is sensed. A VVI pacing mode delivers pacing pulses in a ventricular chamber, senses ventricular R-waves attendant to ventricular depolarization, and inhibits the ventricular pacing pulse when the R-wave is sensed.

One pacing mode is a DDD mode, which includes dual chamber pacing in both an atrial and ventricular chamber, dual chamber sensing in both an atrial and ventricular chamber, and a dual response to sensed events. For example, a sensed P-wave may trigger a ventricular pacing pulse at a programmed atrioventricular (AV) interval (atrial-triggered ventricular pacing), but a sensed R-wave during the AV interval inhibits the ventricular pacing pulse. Available dual chamber pacemakers that are capable of performing DDD pacing are implanted in a subcutaneous pocket and coupled to a transvenous atrial lead and a transvenous ventricular lead carrying atrial pacing and sensing electrodes and ventricular pacing and sensing electrodes, respectively, to enable the dual chamber pacemaker to sense and pace in both chambers.

A fourth letter, R, may be used to designate a rate responsive pacing mode of the pacemaker. In rate responsive pacing, the pacing rate is automatically adjusted in response to a sensor that indicates the metabolic need of the patient, such as a patient activity sensor. An AAIR, VVIR, or DDDR pacing mode is configured to provide rate responsive pacing in the indicated heart chamber(s) by automatically adjusting the pacing lower rate according to a sensor signal indicating the patient's metabolic need.

SUMMARY

In general, the disclosure is directed to implantable medical device (IMD) systems that include multiple implantable medical devices. At least one IMD has a self-configuring control module that enables the IMD to operate in a coordinated manner with another IMD that is implanted in the same patient. An IMD operating in accordance with the techniques disclosed herein establishes the presence of one or more other IMDs and self-configures an appropriate operating mode in response to establishing the presence of another IMD.

In one example, the disclosure provides an IMD system comprising a first implantable medical device; and a second implantable medical device. The first implantable medical device includes a control module configured to control operations of the first implantable medical device according to an operating mode of the first control module. The control module is configured to establish whether the second implantable medical device is present in a patient and self-configure the operating mode of the control module in response to establishing that the second implantable medical device is present.

In another example, the disclosure provides a method performed by an implantable medical device system. The method includes establishing by a control module of a first implantable medical device whether a second implantable medical device is present in a patient and self-configuring an operating mode of the control module in response to establishing that the second implantable medical device is present.

In yet another example, the disclosure provides a non-transitory, computer-readable storage medium storing a set of instructions that when executed by a control module of a first implantable medical device included in an implantable medical device system cause the system to establish whether a second implantable medical device is present in a patient and self-configure an operating mode of the control module in response to establishing that the second implantable medical device is present.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
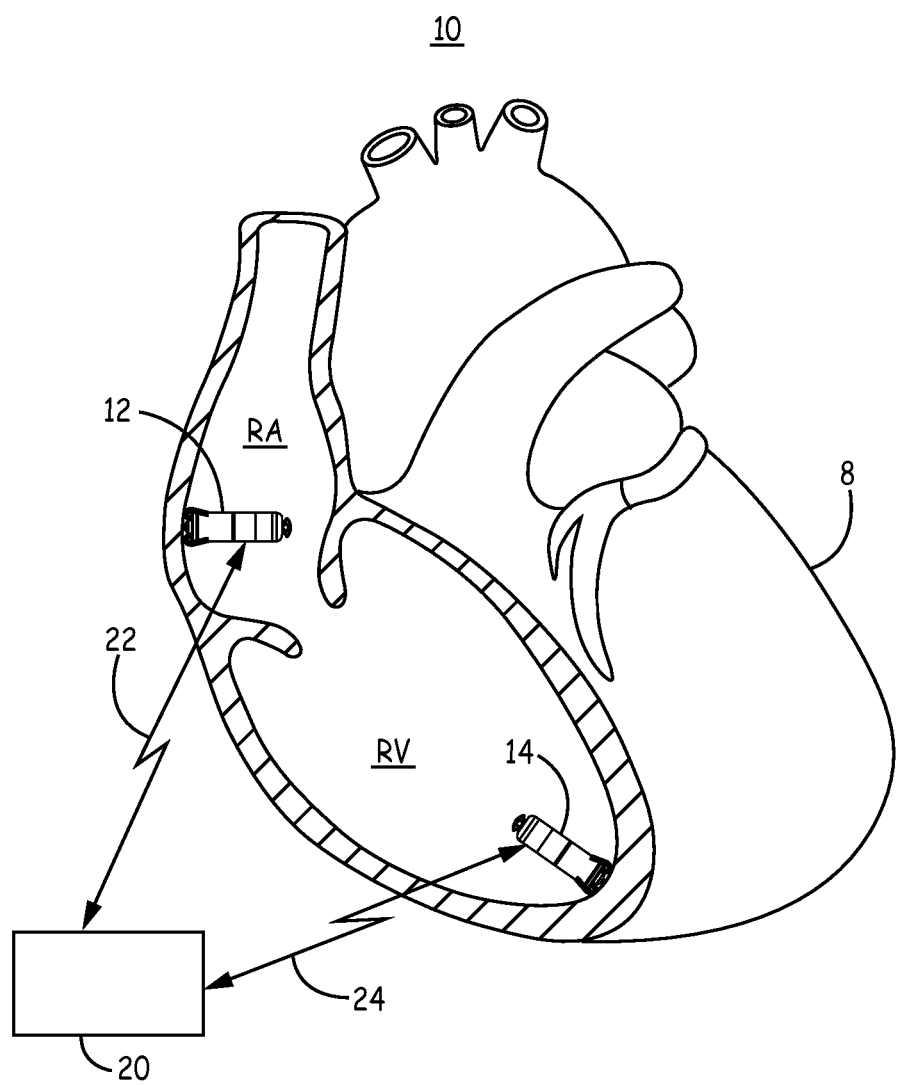
FIG. 1 is a conceptual diagram illustrating an intracardiac pacing system that may be used to sense cardiac electrical signals and provide therapy to a patient's heart.

An implantable medical device (IMD) system is disclosed herein that includes self-configuring IMDs. In various examples, the IMD system includes self-configuring intracardiac pacemakers that do not require transvenous leads but are enabled to provide multi-chamber monitoring and/or therapy delivery functions, such as dual chamber DDD(R) pacing, in a coordinated manner via self-configuring operating modes.

An intracardiac pacemaker included in the system has a control module that self-configures the pacemaker operating mode in response to establishing the presence of other IMDs implanted in the patient in order to provide coordinated and efficient operation between the intracardiac pacemaker and one or more other implanted intracardiac pacemakers and/or other IMDs. When more than one intracardiac pacemaker is present, each pacemaker may self-configure its operating mode to enable multi-chamber sensing and/or therapy delivery functions to be achieved by the separate intracardiac pacemakers in a coordinated manner.

A dual chamber pacemaker positioned in an implant pocket and coupled to transvenous atrial and ventricular leads may be programmed in an AAI(R), VVI(R) or DDD(R) mode according to patient need. The dual chamber pacemaker is able to control the delivery of pacing pulses in both atrial and ventricular chambers because the pacemaker will receive sensed event signals from both chambers and control when a pacing pulse is delivered in both chambers relative to sensed events using the electrodes positioned in both chambers. In other words, the dual chamber pacemaker knows when both sensed and paced events have occurred in both atrial and ventricular pacing channels since all sensing and pacing control is happening in the one device, i.e., the dual chamber pacemaker.

Intracardiac pacemakers have been introduced that are adapted to be implanted wholly within a heart chamber. Elimination of transvenous, intracardiac leads has several advantages. For example, complications due to infection associated with a lead extending from a subcutaneous pacemaker pocket transvenously into the heart can be eliminated. Other complications such as "Twiddler's syndrome", lead fracture or poor connection of the lead to the pacemaker are eliminated in the use of an intracardiac pacemaker.

An intracardiac pacemaker can operate in a single chamber mode, e.g., AAI or VVI, by delivering pacing pulses and inhibiting pacing when an intrinsic event is sensed in the chamber that the pacemaker is implanted in. While some patients may require only single chamber pacing and sensing, patients having AV conduction defects may require a pacing system capable of a DDD pacing mode to provide atrial-synchronized ventricular pacing. As disclosed herein, an IMD system includes intracardiac pacemakers that are configured to establish whether another IMD is present in the patient's body and self-configure its own operating mode from multiple self-configuring operating modes based on the presence or absence of the other IMD(s). When two or more intracardiac pacemakers are present, the ability to configure an operating mode that coordinates the operation of one pacemaker with the operation of the other pacemaker enables the two pacemakers to perform multi-chamber monitoring and therapy delivery operations, e.g., DDD pacing, in an effective and efficient manner.

FIG. 1 is a conceptual diagram illustrating an intracardiac pacing system 10 that may be used to sense cardiac electrical signals and provide therapy to a patient's heart 8. IMD system 10 includes a right atrial (RA) intracardiac pacemaker 12 and a right ventricular (RV) intracardiac pacemaker 14. Pacemakers 12 and 14 are shown as transcatheter intracardiac pacemakers adapted for implantation wholly within a heart chamber, e.g., wholly within the RV, wholly within the left ventricle (LV), wholly within the RA or wholly within the left atrium (LA) of heart 8. In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex. The techniques disclosed herein, however, are not limited to the pacemaker locations shown in the example of FIG. 1 and other positions and relative locations from each other are possible.

Pacemakers 12 and 14 are reduced in size and generally cylindrical in shape to enable transvenous implantation via a delivery catheter. In other examples, pacemakers 12 and 14 may be positioned at any other location inside or outside heart 8, including epicardial locations. For example, pacemaker 12 may be positioned outside or within the right atrium or left atrium to provide respective right atrial or left atrial pacing. Pacemaker 14 may be positioned outside or within the right ventricle or left ventricle to provide respective right ventricular or left ventricular pacing.

Pacemakers 12 and 14 are each capable of producing electrical stimulation pulses, i.e., pacing pulses, delivered to heart 8 via one or more electrodes on the outer housing of the pacemaker. RA pacemaker 12 is configured to sense an intracardiac electrogram (EGM) signal in the RA using the housing based electrodes and deliver RA pacing pulses. RV pacemaker 14 is configured to sense an EGM signal in the RV using one or more housing based electrodes and deliver RV pacing pulses.

Depending on individual patient need, RA pacemaker 12 may be implanted first, and RV pacemaker 14 may be implanted at a later time after the patient develops a need for ventricular pacing, e.g., if the patient develops AV conduction defects. In other examples, the patient may receive the RV pacemaker 14 first and later receive RA pacemaker 12, or the patient may receive both RA pacemaker 12 and RV pacemaker 14 during the same implant procedure.

The RA pacemaker 12 and the RV pacemaker 14 are configured to detect the presence (or absence) of the other pacemaker and automatically select a solo operating mode or a duo operating mode based on whether the other pacemaker is present or not. Each of the RA pacemaker 12 and RV pacemaker 14 include a control module that controls functions performed by the respective pacemaker. The control module is enabled to self-configure the solo or duo operating mode in response to the presence or absence of the other pacemaker.

As will be described in greater detail below, each pacemaker 12 and 14 includes features and capabilities that are enabled or disabled automatically when an operating mode is self-configured. In some cases, the operating mode is adjusted automatically by the pacemaker control module based on the presence or absence of other types of implanted medical devices, such as an implantable cardioverter defibrillator (ICD), implantable ECG monitor, or other cardiac monitoring or therapy delivery device.

Pacemaker 12 and 14 are each capable of bidirectional wireless communication with an external device 20. External device 20 may be a programmer used by a clinician or other user in a medical facility, a home monitor located in a patient's home, or a handheld device. Aspects of external device 20 may generally correspond to the external programming/monitoring unit disclosed in U.S. Pat. No. 5,507,782 (Kieval, et al.), hereby incorporated herein by reference in its entirety.

External device 20 establishes a wireless radio frequency (RF) communication link 22 with RA pacemaker 12 and wireless RF communication link 24 with RV pacemaker 14 using a communication protocol that appropriately addresses the targeted pacemaker 12 and 14. An example RF telemetry communication system that may be implemented in system 10 is generally disclosed in U.S. Pat. No. 5,683,432 (Goedeke, et al.), incorporated herein by reference in its entirety.

External device 20 may be used for retrieving data from pacemakers 12 and 14 and for sending data to pacemakers 12 and 14. Examples of retrieved data include physiological signals such as RA or RV EGM signals, therapy delivery data such as a history of pacing frequency, results of device diagnostic testing, current operating mode and control parameters or other data stored by the pacemaker.

Data sent to pacemakers 12 and 14 may include programmable control parameters. The self-configuring control module may establish which programmable control parameters and corresponding settings are available for a user to program based on the selected operating mode. The pacemaker 12 or 14 may transmit operating mode data to external device 20, e.g., in response to an interrogation command from external device 20, such that external device 20 displays user programmable parameters and settings relevant to the operating mode.

Pacemaker 12 and pacemaker 14 may or may not be configured to communicate directly with each other. For example, neither RA pacemaker 12 nor RV pacemaker 14 may be configured to initiate an RF communication session with the other device. Both pacemakers 12, 14 may be configured to periodically "listen" for a valid "wake up" telemetry signal from external device 20 and power up its own telemetry module to establish a communication link 22 or 24 in response to a valid telemetry signal (or go back to "sleep" if no valid telemetry signal is received). However, pacemakers 12 and 14 may not be configured to transmit a "wake up" signal to the other pacemaker to initiate a communication session. In other examples, the pacemakers 12 and 14 may be configured to communicate with each other, but in order to conserve battery life of the intracardiac pacemakers, communication may be minimized. As such, communication may not occur on a beat-by-beat basis between the RA pacemaker 12 and RV pacemaker 14 for communicating when the other pacemaker is sensing cardiac events or when it is delivering pacing pulses.

A subcutaneously implanted dual chamber pacemaker is generally coupled to transvenous leads carrying electrodes positioned in both the RA and the RV. When a pacemaker is coupled to electrodes positioned in both chambers, P-wave sense signals and R-wave sense signals are available to control both atrial and ventricular pacing pulses in a coordinated manner with the sensed events. In system 10 of FIG. 1, RA pacemaker 12 and RV pacemaker 14 may not be enabled to communicate by wireless RF telemetry on a beat-by-beat basis. The pacemaker in one heart chamber (RA or RV) does not receive communication signals transmitted directly from the other pacemaker in the other heart chamber indicating when the other pacemaker has sensed a cardiac event or when it has delivered a pacing pulse. In accordance with techniques disclosed herein, however, RV pacemaker 14 may be configured to sense far-field (FF) P-waves and FF atrial pacing pulses from the RV EGM signal. RV pacemaker 14 may therefore be enabled to indirectly determine when RA pacemaker 12 delivers a pacing pulse and/or when RA pacemaker 12 has most likely sensed a P-wave. Likewise, RA pacemaker 12 may be configured to sense FF ventricular events, including R-waves and/or ventricular pacing pulses.

As will be described herein, in a duo operating mode, the two pacemakers 12 and 14 may be configured to determine if a pacing pulse has been delivered by the other pacemaker and/or when an evoked or intrinsic event has been sensed by the other pacemaker such that the two individual pacemakers 12 and 14 can operate in a coherent, coordinated manner for delivering dual chamber pacing. In this way, a DDD(R) pacing mode is achieved by the operation of the two separate intracardiac pacemakers 12 and 14 without requiring direct communication, e.g., wired signals or wireless RF communication signals, between the two pacemakers 12 and 14 on a beat-by-beat basis.

The control module of at least a first one of the two pacemakers 12 and 14 is configured to determine when the second pacemaker is sensing an event and/or delivering a pacing pulse based on sensed event signals produced by a sensing module of the first pacemaker. In addition to coordinating dual chamber pacing, the self-configured operating mode sets the status of other pacemaker functions as being enabled, disabled or otherwise adjusted based on the presence or absence of the other pacemaker, or another implanted device.

Figure 2A:
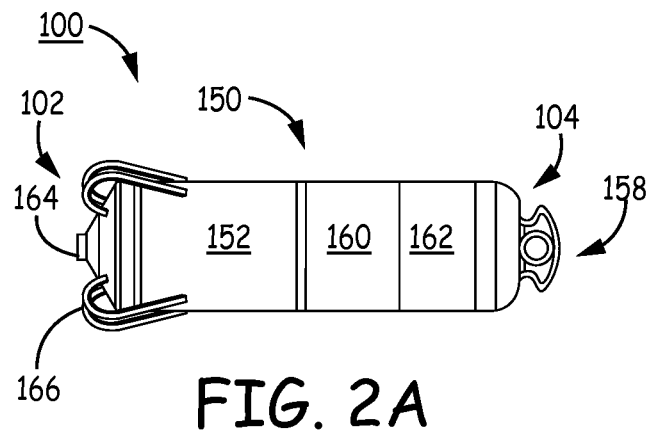
FIG. 2A is a conceptual diagram of an intracardiac pacemaker.

FIG. 2A is a conceptual diagram of an intracardiac pacemaker 100 that may correspond to RA pacemaker 12 or RV pacemaker 14 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced through a delivery tool such as a catheter and placed against a target pacing site.

Electrodes 162 and 164 may be positioned on or as near as possible to respective proximal and distal ends 104 and 102 to increase the inter-electrode spacing between electrodes 162 and 164. Electrodes 162 and 164 form an anode and cathode pair for bipolar cardiac pacing and sensing. Relatively greater inter-electrode spacing will increase the likelihood of sensing FF signals that are used by the pacemaker 100 for detecting the presence of another pacemaker in another heart chamber and/or in coordinating pacing pulse delivery with a paced or sensed event in another heart chamber. For example, an increased inter-electrode spacing between electrodes 162 and 164 when pacemaker 100 is used as an RV pacemaker will improve the likelihood of reliably sensing FF P-waves.

In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162.

The housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of active fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 is located at the proximal end 104 of pacemaker 100 and is configured to connect to a delivery device, such as a catheter, used to position pacemaker 100 at an implant location during an implantation procedure, for example within a heart chamber.

A reduced size of pacemaker 100 enables implantation wholly within a heart chamber. In FIG. 1, RA pacemaker 12 and RV pacemaker 14 may have different dimensions. For example, RA pacemaker 12 may be smaller in volume than pacemaker 14, e.g., by reducing battery size, to accommodate implantation in the smaller heart chamber. As such, it is recognized that pacemaker 100 may be adapted in size, shape, electrode location or other physical characteristics according to the heart chamber in which it will be implanted.

Figure 2B:
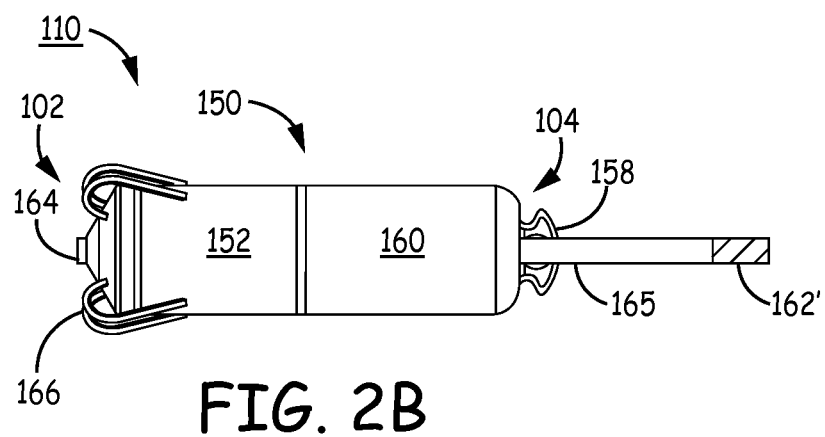
FIGS. 2B and 2C are conceptual diagrams of alternative embodiments of an intracardiac pacemaker.

FIG. 2B is a conceptual diagram of an alternative embodiment of an intracardiac pacemaker 110. Pacemaker 110 includes a housing 150, control assembly 152, battery assembly 160, fixation member 166 and electrode 164 along a distal end 102, and may include a delivery tool interface 158 along the proximal end 104 as described above in conjunction with FIG. 2A. Pacemaker 110 is shown to include an electrode 162' extending away from housing 150 along an extender 165. As such, instead of carrying a pair of electrodes along the housing 150, which limits the maximum possible inter-electrode spacing, an extender 165 may be coupled to the housing 150 for positioning an electrode 162' at an increased inter-electrode distance from distal tip electrode 164. Reference is made to U.S. Patent Application No. 62/025,690, filed provisionally on Jul. 17, 2014, incorporated herein by reference in its entirety, for examples of an intracardiac pacemaker having increased inter-electrode spacing between electrodes.

Figure 2C:
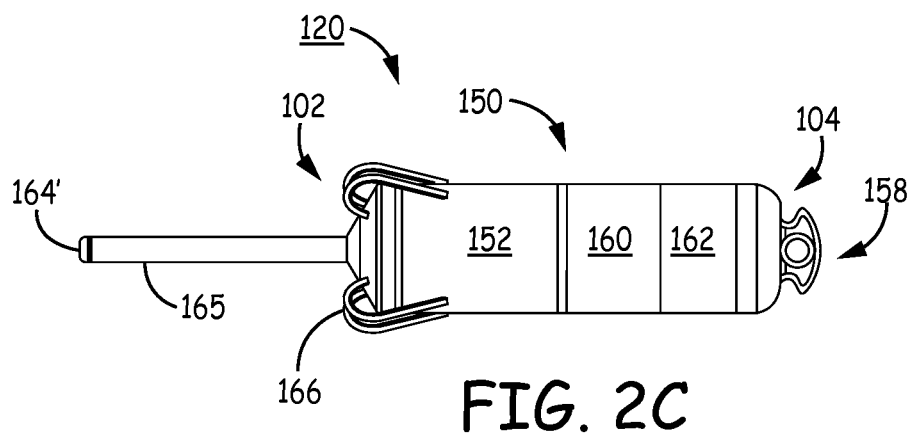

FIG. 2C is a conceptual diagram of an alternative embodiment of intracardiac pacemaker 120 having extender 165 coupled to the distal end 102 of pacemaker housing 150 to extend distal electrode 164' away from electrode 162 positioned along housing 150 near or at proximal end 104. Extender 165 shown in FIGS. 2B and 2C is an insulated electrical conductor that electrically couples electrode 162' (FIG. 2B) or electrode 164' (FIG. 2C) to pacemaker circuitry. Pacemaker 120 having an insulated, electrically conductive extender 165 for increasing the inter-electrode spacing may correspond generally to the implantable device and flexible conductor disclosed in commonly-assigned, pre-grant U.S. Publication No. 2013/0035748 (Bonner, et al.), hereby incorporated herein by reference in its entirety.

Figure 3:
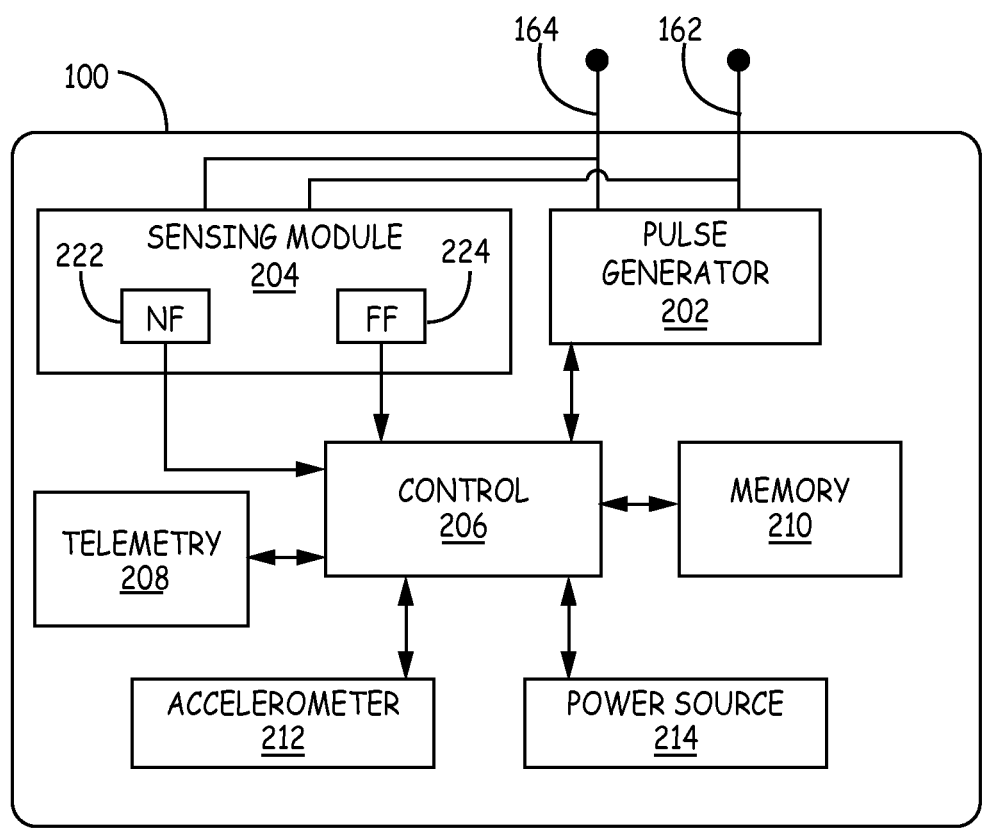
FIG. 3 is a functional block diagram of an example configuration of the intracardiac pacemaker shown in FIG. 2A, 2B or 2C.

FIG. 3 is a functional block diagram of an example configuration of pacemaker 100 shown in FIG. 2A (or pacemakers 110 or 120 of FIGS. 2B and 2C), and may correspond generally to the functional circuitry included in both RA pacemaker 12 and RV pacemaker 14. Pacemaker 100 includes a pulse generator 202, a sensing module 204, a control module 206, memory 210, telemetry module 208 and a power source 214.

As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. The particular form of software, hardware and/or firmware employed to implement the functionality disclosed herein will be determined primarily by the particular system architecture employed in the pacemaker. Providing software, hardware, and/or firmware to accomplish the described functionality in the context of any modern IMD, given the disclosure herein, is within the abilities of one of skill in the art.

Each of RA pacemaker 12 and RV pacemaker 14 may include similar modules as represented by the pacemaker 100 shown in FIG. 3; however it is understood that the modules may be configured according to the functionality of the separate RA and RV pacemakers 12 and 14 as disclosed herein. For example, when pacemaker 100 is a RA pacemaker 12, control module 206 is enabled to self-configure the solo and duo operating modes of the RA pacemaker as disclosed herein. Likewise, when pacemaker 100 is a RV pacemaker 14, control module 206 is enabled to self-configure the solo and duo operating modes of the RV pacemaker as disclosed herein. Adaptations of the hardware, firmware or software of the various modules necessary to meet the described functionality of the intracardiac pacemakers positioned in different heart chambers as disclosed herein is understood to be included in the various modules.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by pacemaker 100 may be implemented in control module 206 executing instructions stored in associated memory 210 and relying on input from sensing module 204.

Pulse generator 202 generates electrical stimulation pulses that are delivered to heart tissue via electrodes 162 and 164. Electrodes 162 and 164 may be housing-based electrodes as shown in FIG. 2A, but one or both electrodes 162 and 164 may alternatively be carried by an insulated, electrical conductor extending away from the pacemaker housing as described in conjunction with FIGS. 2B and 2C.

Pulse generator 202 may include one or more capacitors and a charging circuit to charge the capacitor(s) to a programmed pacing pulse voltage. At appropriate times, as controlled by a pace timing and control circuit included in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,597,782 (Kieval, et al.) and in commonly assigned U.S. Pat. No. 8,532,785 (Crutchfield, et al.), incorporated herein by reference in its entirety, may be implemented in pacemaker 100 for charging a pacing capacitor to a predetermined pacing pulse amplitude under the control of control module 206 and delivering a pacing pulse.

Control module 206 controls pulse generator 202 to deliver a pacing pulse in response to expiration of a pacing timing interval according to programmed therapy control parameters stored in memory 210. Control module 206 self-configures an operating mode based on establishing whether another pacemaker is present or not. Within a given operating mode, one or more pacing modes may be available, each defined by an appropriate set of control parameters. The pace timing and control circuit included in control module 206 sets various timing intervals, often referred to as escape intervals, used for controlling the timing of pacing pulses relative to a paced or sensed event. Upon expiration of a pacing timing interval, a pacing pulse is delivered. If a cardiac event is sensed during the pacing timing interval, the scheduled pacing pulse may be inhibited, and the pacing timing interval may be restarted.

For example, RA pacemaker 12 (FIG. 1) may operate by starting a lower rate pacing escape interval in response to an intrinsic sensed P-wave or an atrial pacing pulse. If the escape interval expires prior to sensing a next intrinsic P-wave, an atrial pacing pulse is delivered. If an intrinsic P-wave is sensed by sensing module 204, the escape interval is restarted. Similarly, RV pacemaker 14 (FIG. 1) may set a lower rate pacing escape interval in response to an intrinsic sensed R-wave or ventricular pacing pulse. If the escape interval expires, a ventricular pacing pulse is delivered by pulse generator 202. If an R-wave is sensed during the escape interval, outside any applicable blanking or refractory intervals, the escape interval is restarted.

Sensing module 204 includes cardiac event detectors for receiving cardiac EGM signals developed across electrodes 162 and 164. A cardiac event is sensed by sensing module 204 when the EGM signal crosses a sensing threshold, which may be an auto-adjusting sensing threshold, of a cardiac event detector. In response to a sensing threshold crossing, sensing module 204 passes a sensed event signal to control module 206. RA pacemaker 12 may be programmed with a sensing threshold appropriate for sensing P-waves attendant to the depolarization of the atria. RV pacemaker 14 may be programmed with a sensing threshold appropriate for sensing R-waves attendant to the depolarization of the ventricles.

The terms "sensed cardiac events" or "sensed events" as used herein refers to events sensed by sensing module 204 in response to the EGM signal crossing a sensing threshold, which may be an amplitude threshold, a frequency threshold, a slew rate threshold, or any combination thereof. Sensed cardiac events may include intrinsic events and evoked events, both of which may also be referred to as "depolarization events" since both intrinsic and evoked sensed cardiac events are associated with depolarization of the myocardium, either an intrinsic depolarization or a pacing evoked depolarization of the myocardium, respectively. Intrinsic events are events arising in the heart in the absence of a pacing pulse. Intrinsic events include intrinsic P-waves, such as sinus P-waves originating from the sinoatrial node of the heart, and intrinsic R-waves, such as sinus R-waves conducted from the atria via the atrioventricular node. Intrinsic events can also include non-sinus intrinsic events, such as premature atrial contractions (PACs) or premature ventricular contractions (PVCs) that arise intrinsically from the heart but are ectopic in origin.

Sensed intrinsic events may include near-field (NF) events and far-field (FF) events. NF events are events that are occurring in the heart chamber where the bipolar sensing electrodes 162 and 164 are positioned. FF events are events occurring in a different heart chamber, where electrodes 162 and 164 are not positioned. As described herein, pacemaker 100 may sense NF and FF events for monitoring the patient's heart and/or for controlling pacing pulse delivery. As such, sensing module 204 may include a NF sensing channel 222 for sensing NF events and providing NF sensed event signals to control module 206 and a FF sensing channel 224 for sensing FF events and providing FF sensed event signals to control module 206.

For example, the RA pacemaker 12 may sense both NF P-waves and FF R-waves. A P-wave sensing threshold may be used by NF sensing channel 222, and a different R-wave sensing threshold may be used by FF sensing channel 224 and applied to the same EGM signal received by electrodes 162 and 164 to distinctly sense NF P-waves and FF R-waves. The threshold may be applied to a signal amplitude or other waveform morphology features to differentiate NF and FF signals. Additionally or alternatively, different sensing windows, refractory windows, and/or blanking intervals may be applied by control module 206 to discriminate between NF P-waves and FF R-waves based on timing. For example, a refractory or blanking interval may be set by the RA pacemaker control module 206 following a P-wave sensed event signal or an atrial pacing pulse so that any event sensed during the refractory or blanking interval may be identified as a FF R-wave and is not used to reset a lower rate pacing escape interval and therefore ignored for determining the atrial intrinsic rate and for controlling atrial pacing. Alternatively, a sensed FF R-wave could also be used to set an escape interval for controlling the timing of the next atrial pacing pulse. The sensed FF R-wave may be used by the RA pacemaker for monitoring purposes, such as monitoring the AV conduction time between the atria and the ventricles.

Far-field P-waves may be present on the ventricular EGM signal sensed by RV pacemaker 14. FF P-waves are typically much smaller in amplitude than NF R-waves and are therefore distinguishable from R-waves based on amplitude. An R-wave sensing threshold can be set greater than an expected FF P-wave amplitude so that R-waves are sensed when the EGM signal received by electrodes 162 and 164 crosses the R-wave sensing threshold in NF sensing channel 22. FF P-waves may be sensed by FF sensing channel 224 of the RV pacemaker using a different sensing threshold than the NF R-wave sensing threshold, and optionally using a designated P-wave sensing window applied by control module 206. FF P-wave sense signals received from FF sensing channel 224 may be used by control module 206 to deliver atrial-synchronized ventricular pacing as further described below and as generally disclosed in the above-incorporated U.S. Patent Application No. 62/025,690, filed provisionally on Jul. 17, 2014.

As indicated above, events sensed by sensing module 204 may include evoked events. An evoked event is the signal attendant to depolarization of the myocardial tissue caused by a pacing pulse. Evoked events may be sensed in order to verify capture of a pacing pulse. For example, the RA pacemaker 12 may be configured to deliver a RA pacing pulse, set a blanking interval during the pacing pulse to prevent saturation of the sensing module 202 due to the pacing pulse, then set a capture detection window. A P-wave sensed during the capture detection window is sensed as an evoked P-wave and is evidence that the pacing pulse successfully captured the atrium. The RA pacemaker 12 may sense both intrinsic P-waves and evoked P-waves. FF evoked R-waves caused by delivering of a ventricular pacing pulse by RV pacemaker 14 may also be sensed by FF sensing channel 224. FF evoked P-waves caused by an atrial pacing pulse delivered by RA pacemaker 12 may be sensed by the FF sensing channel 224 in RV pacemaker 14.

Sensed events may further include sensing of a pacing pulse delivered by an intracardiac pacemaker in another heart chamber. For example, RA pacing pulses delivered by RA pacemaker 12 may have a relatively high amplitude on the ventricular EGM signal received by the sensing module 204 of RV pacemaker 14. Similarly, a RV pacing pulse delivered by RV pacemaker 14 may appear as a FF signal on the RA EGM signal received by RA pacemaker 12. Sensing module 204 may be configured to produce FF pacing pulse sense signals that are passed to control module 206 so that one pacemaker can identify the time that the other pacemaker in another heart chamber has delivered a pacing pulse.

For example, in RV pacemaker 14, FF sensing channel 224 of sensing module 204 may be configured to sense FF atrial pacing pulses. As described in greater detail below, FF atrial pacing pulse sense signals provided to control module 206 are used to control the timing of ventricular pacing pulses during atrial-synchronized ventricular pacing. Depending on the frequency characteristics of the sensing module 204 and the relative orientation of the pacemakers 12 and 14, and their respective electrodes, the RA pacing pulse may or may not be sensed by the RV sensing module 204.

Sensing module 204 may include multiple sensing channels for intentionally sensing both NF and FF events, including NF and FF intrinsic events, NF and FF evoked events, and FF pacing pulse events. By intentionally sensing FF events, control module 206 can control pacemaker 100 to operate in a coordinated manner with a pacemaker in another heart chamber.

For example, RV pacemaker 14 may include a NF channel 222 for sensing NF R-waves and a FF channel 224 for sensing FF atrial pacing pulses delivered by RA pacemaker 12 and/or FF P-waves. The NF and FF sensing channels 222 and 224 may have different band pass frequencies and different sensing thresholds. FF sensing channel 224 may include one or more cardiac event detectors or "sub-channels" to separately sense different FF events, e.g., FF P-waves and FF atrial pacing pulses. The same EGM signal acquired across electrodes 162 and 164 is applied to all sensing channels, but different events are sensed based on the different bandpass frequencies and sensing thresholds selected to enhance sensing of a desired NF or FF event.

In response to a sensing threshold crossing, sensing module 204 passes sensed event signals to control module 206. Sensed event signals may include FF pacing pulse sensed event signals, FF R-wave or P-wave sensed event signals (e.g., FF P-waves in the case of RV pacemaker 14 and FF R-waves in the case of RA pacemaker 12), and NF R-wave or P-wave sensed event signals (NF R-waves in the case of RV pacemaker 14 and NF P-waves in the case of RA pacemaker 12).

Control module 206 uses the sensed event signals to control pulse generator 202 in a desired pacing mode as described in greater detail below. Additionally or alternatively, FF pacing pulse sensed event signals may be used by control module 206 to establish the presence of an intracardiac pacemaker in another heart chamber.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores timing intervals, counters, or other data used by control module 206 to control the delivery of pacing pulses by pulse generator 202 according to the currently configured operating mode.

Pacemaker 100 may further include an accelerometer 212 for producing a patient activity signal passed to control module 206. Accelerometer 212 may be embodied as a piezoelectric crystal for producing a signal correlated to body motion. The use of an accelerometer in an intracardiac device for obtaining a patient activity signal is generally disclosed in U.S. patent application Ser. No. 14/174,514 filed on Feb. 6, 2014 (Nikolski, et al.), hereby incorporated herein by reference in its entirety.

The accelerometer signal is used to determine a sensor-indicated rate (SIR) used to set a pacing escape interval for controlling the pacing rate to meet the metabolic demand of the patient. The atrial pacing escape interval or the ventricular pacing escape interval during single chamber pacing modes is initially set according to a programmed lower or base pacing rate to provide bradycardia pacing. The lower or base pacing rate may be automatically adjusted to provide rate responsive pacing based on a sensor signal indicative of the patient's metabolic demand, such as a signal from accelerometer 212. The use of a patient activity signal for providing rate-responsive pacing is generally disclosed in U.S. Pat. No. 7,031,772 (Condie, et al.), incorporated herein by reference in its entirety.

The signal produced by accelerometer 212 may additionally or alternatively be used by control module 206 to detect motion of another heart chamber for monitoring purposes. For example, when pacemaker 100 is positioned in the RA as the RA pacemaker 12 in FIG. 1, a motion artifact on the accelerometer signal due to ventricular contraction at the onset of the ventricular systolic ejection phase, may be identified as a surrogate for sensing FF R-waves as evidence of ventricular depolarization. A time interval between an atrial event, paced or sensed, and the surrogate ventricular depolarization signal identified from the accelerometer signal may be measured as an AV conduction time and used for AV conduction time monitoring by the RA pacemaker 12. As described below, AV conduction time monitoring by RA pacemaker 12 may be enabled during a solo operating mode to determine a need for RV pacemaker 14 based on increased AV conduction time.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data via a radio frequency (RF) communication link. RF communication with external device 20 (FIG. 1), may occur in the Medical Implant Communication Service (MICS) band, the Medical Data Service (MEDS) band, or other frequency bands, including, but not limited to a 2.4 GHz industrial, scientific and medical (ISM) band for Bluetooth and IEEE 802.11 b/g/n standards. Telemetry module 208 may be capable of bi-directional communication with external device 20 over a wide range of distances, e.g., up to approximately 10 meters. In other examples, telemetry communication may require the use of a programming head placed in proximity of pacemaker 100 to facilitate data transfer.

Figure 4:
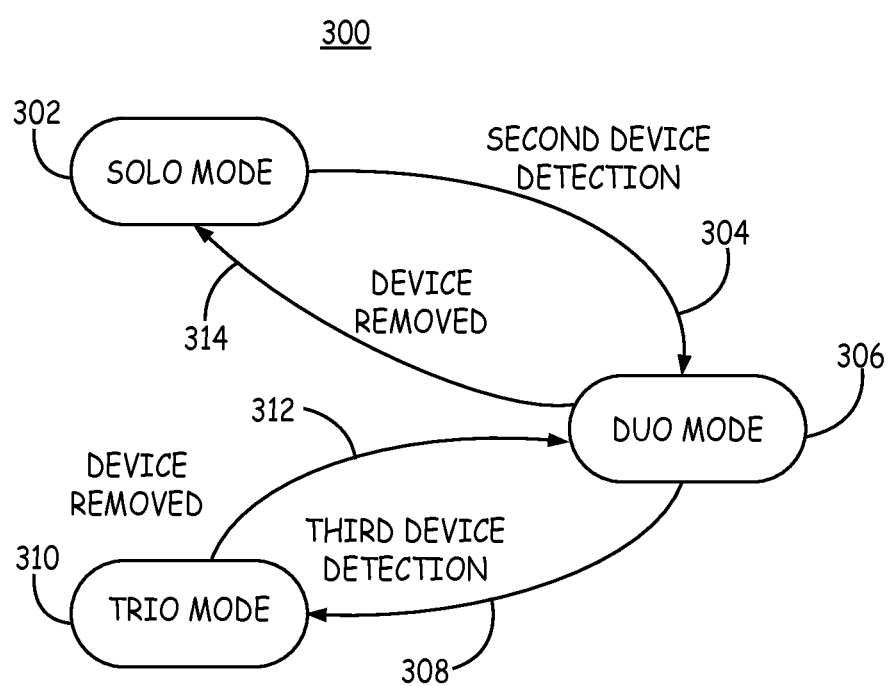
FIG. 4 is a conceptual diagram of self-configuring operating modes of an intracardiac pacemaker.

FIG. 4 is a conceptual diagram 300 of the self-configuring operating modes of an intracardiac pacemaker 100 included in an IMD system, such as system 10 of FIG. 1. The IMD system 10 includes at least one intracardiac pacemaker 100 and may include two or more intracardiac pacemakers, e.g. RA pacemaker 12 and RV pacemaker 14 and an LV pacemaker. Each pacemaker may be implantable wholly within a heart chamber and therefore capable of delivering cardiac pacing in a single chamber using an electrode bipole, e.g., electrodes 162 and 164. In some examples, the IMD system includes at least one intracardiac pacemaker and may include one or more other cardiac monitoring or therapy delivery devices such as an ICD or subcutaneous ECG monitor.

A first intracardiac pacemaker 100 is implanted and self-configures in a solo operating mode as indicated by state 302. The first intracardiac pacemaker operating in a solo mode establishes whether a second intracardiac pacemaker is present. The presence of a second intracardiac pacemaker may be established based on a signal received from an external device 20 notifying the first pacemaker that the second pacemaker has been implanted. Alternatively, the presence of a second intracardiac pacemaker may be established based on sensing FF pacing pulse signals by the sensing module 204 of the first pacemaker 100.

If a second pacemaker is detected as indicated by transition 304, the first pacemaker reconfigures itself (or self-configures) to a duo operating mode in state 306. The second pacemaker likewise establishes the presence of the first pacemaker and self-configures in a duo operating mode in state 306. The second pacemaker being implanted may receive a notification signal from the external device 20 indicating the presence of the first pacemaker. The second pacemaker automatically configures itself in the duo operating mode in state 306 in response to the command. Alternatively, the second pacemaker, upon being implanted, may sense FF pacing pulses being delivered by the first pacemaker from the EGM signal received by the second pacemaker and automatically configure itself in the duo operating mode 306.

In one example, the first device implanted is the RA pacemaker 12 and the second device implanted is the RV pacemaker 14. In another example, the first device is the RV pacemaker 14 and the second device is the RA pacemaker 12. In yet another example the first device implanted is either a RA pacemaker or a LV pacemaker and the second device is the other of the RA pacemaker and the LV pacemaker.

The time between implanting the first pacemaker and the second pacemaker may vary between patients. In some cases both pacemakers may be implanted in the same procedure such that both devices self-configure in the duo operating mode immediately or soon after implantation. In other examples, implantation of the second pacemaker may occur days, weeks, months or even years after the first pacemaker.

In some examples a third intracardiac pacemaker may be detected by the first and second pacemakers, as indicated by transition 308. The first and second pacemakers may automatically switch from a duo mode to a trio mode in state 310. Likewise, the third intracardiac pacemaker will self-configure in the trio mode 310 based on detection of the first and second pacemakers, automatically in response to FF sensed pacing pulses or in response to a notification received from an external device. In one example, a trio mode enables an intracardiac pacemaker 100 to sense FF events in one or two other heart chambers and use the FF events to monitor the patient's heart rhythm and/or trigger or inhibit pacing pulses delivered in the heart chamber that the pacemaker 100 is implanted in, based on the FF events.

In some cases, another device that is not an intracardiac pacemaker may already be present or implanted after an intracardiac pacemaker. If another IMD other than an intracardiac pacemaker 100 is present, the intracardiac pacemaker 100 may modify its self-configured solo, duo, or trio mode to operate in a manner that is desired when the other IMD is present. As such, the solo, duo and trio operating modes may refer to operating modes that enable one, two or three intracardiac pacemakers to operate appropriately alone or cooperatively with one or more other intracardiac pacemakers. Each of the solo, duo and trio operating modes may be modified based on the presence of another implantable device other than an intracardiac pacemaker. For example, a modified solo, duo or trio operating mode may disable an intracardiac pacemaker function to eliminate redundant functions that can be performed by another IMD and thereby conserve battery energy of the intracardiac pacemaker.

In other examples, a modified solo, duo or trio operating mode of intracardiac pacemaker 100 may enable a feature or function available in the pacemaker that is not used unless another IMD is present. To illustrate, an intracardiac pacemaker 100 operating in solo mode or operating in a duo mode when another intracardiac pacemaker is present may modify its solo or duo mode when an ICD is implanted include anti-tachycardia pacing (ATP) delivery. ATP delivery by an IMD system may be undesired unless defibrillation capabilities are available. When an ICD is added to the IMD system, any intracardiac pacemakers present may modify their current operating mode to include ATP.

Implantable devices may be added or removed from the IMD system present in a patient. As such, if three intracardiac pacemakers are present and operating in the trio mode 310, one pacemaker may be removed or disabled as indicated by transition 312. In some cases, an implanted pacemaker may not be physically removed from the patient but may reach battery end-of-life or be "turned off" such that it is no longer functional in the implanted IMD system or is no longer delivering pacing therapy. The remaining two devices will detect the removal of the second device from the system, either automatically based on sensed EGM signals or by receiving a notification from an external device. The remaining pacemakers will self-configure in the duo operating mode in state 306. If another pacemaker is removed from the system as indicated by transition 314, the remaining pacemaker detects the removal and self-configures itself in the solo operating mode in state 302.

The solo mode in state 302, duo mode in state 306, trio mode in state 310 and so on for each intracardiac pacemaker present in an IMD system may be uniquely defined for the given pacemaker and for a given combination of pacemakers. For example, if the RA pacemaker 12 is present initially and operating in the solo mode in state 302, it may self-configure to a duo operating mode including one set of features and control parameters in response to detecting the presence of a second pacemaker, such as RV pacemaker 14 but switch to a different duo mode of operation including a different set of features and control parameters in response to detecting the presence of a different pacemaker such as a LA pacemaker. As such, for each intracardiac pacemaker that may be introduced to the overall IMD system a unique solo mode of operation may be defined in addition to one or more duo operating modes each defined according to the type and/or location of the second pacemaker that is implanted, one or more trio modes each defined according to the type and location of the third pacemaker that is implanted, and so on.

While the presence of up to three implantable pacemakers is depicted in FIG. 4, the methods disclosed herein may be extended to four intracardiac pacemakers operating in each of the four heart chambers, in which case a quad mode may be defined for each pacemaker. Each intracardiac pacemaker may further include self-configured, modified operating modes used when other types of IMDs are present, such as a modified solo operating mode with an ICD present, modified duo operating mode with an ICD present, etc.

Figure 5:
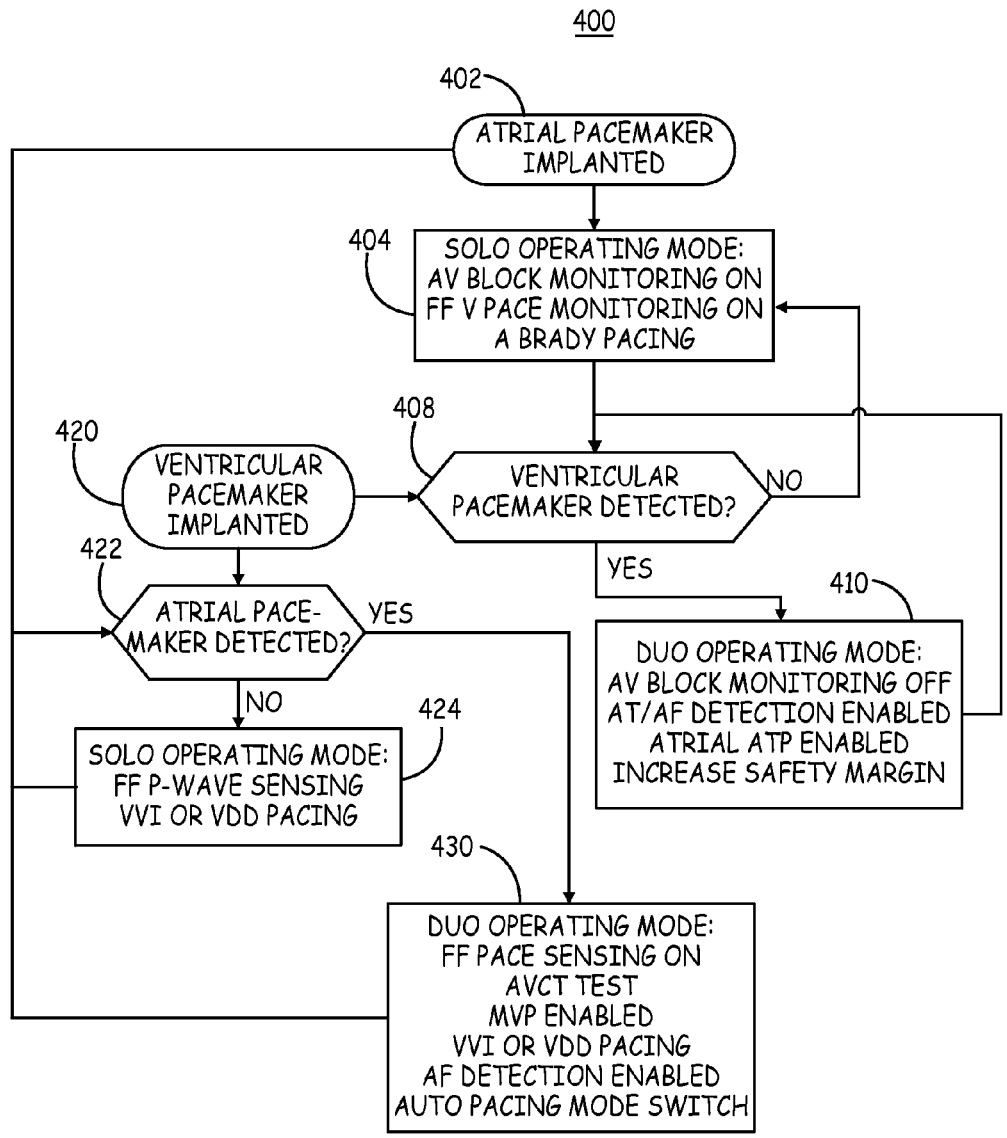
FIG. 5 is a flow chart of the operation of an intracardiac atrial pacemaker and an intracardiac ventricular pacemaker both enabled to automatically configure solo and duo operating modes according to the presence or absence of the other pacemaker.

FIG. 5 is a flow chart 400 of the operation of an intracardiac atrial pacemaker 12 and an intracardiac ventricular pacemaker 14 both enabled to automatically configure respective solo and duo operating modes according to the presence or absence of the other pacemaker. In one illustrative example, an intracardiac atrial pacemaker, such as RA pacemaker 12, is implanted first at block 402. Many patients may require bradycardia atrial pacing without requiring ventricular pacing due to normal atrioventricular conduction. The atrial pacemaker is initially configured in the solo mode as indicated at block 404.

The atrial pacemaker 12 may be provided by the manufacturer in the solo operating mode by default or may self-configure in the solo mode in response to a notification from a programmer (or other external device) indicating the atrial pacemaker is the sole pacemaker, i.e., no other intracardiac pacemakers are previously or simultaneously implanted. The solo operating mode may be defined by a combination of pacemaker features and control parameters that control both monitoring functions of the atrial pacemaker and therapy delivery functions of the atrial pacemaker.

For example, in a solo operating mode, the atrial pacemaker 12 may be configured to operate as single chamber atrial pacemaker delivering bradycardia pacing in an AAI or AAIR pacing mode. As used herein, the "operating mode" refers to the overall functions of the pacemaker which may include physiological signal monitoring, bradycardia pacing, one or more other types of cardiac stimulation therapy delivery such as ATP or cardiac resynchronization therapy (CRT), self-diagnostic testing and other device functions. As such, the bradycardia pacing mode designated by the three or four letter sequence indicating which chamber bradycardia pacing is delivered in and which chamber(s) cardiac events are sensed in for use in controlling the timing of the bradycardia pacing pulses is one aspect of the overall operating mode. One or more programmable pacing modes may be available within a given solo or duo operating mode.

In a solo operating mode configured at block 404, AV conduction block monitoring is turned on in one example. AV conduction block monitoring is turned on by enabling the atrial intracardiac pacemaker to sense FF R-waves for measuring time intervals between NF P-wave sensed event signals and FF R-wave sensed event signals received by the control module from the sensing module. An absence or latency of FF R-waves is an indication of the development of AV block and may indicate a need for an intracardiac ventricular pacemaker. AV block monitoring may therefore be enabled, i.e., turned "on", in the solo mode at block 404. Data relating to evidence of AV block based on FF R-wave sensing may be stored by the atrial pacemaker and transmitted to the external device (a programmer, home monitor, or other external device 20 as shown in FIG. 1) to alert a clinician or other user to the possible need for ventricular pacing.

The solo operating mode configured at block 404 further includes an atrial (A) bradycardia pacing mode, e.g., AAI or AAIR mode. In some examples, no other therapies are enabled in the solo operating mode besides single chamber pacing. Even though the atrial pacemaker may be configured for sensing FF R-waves in the solo operating mode, the pacing mode is designated as the AAI(R) mode since only NF P-waves inhibit a scheduled atrial pacing pulse and only NF P-waves or atrial pacing pulses (but not FF R-waves) are used to start atrial pacing escape intervals. The atrial pacemaker is configured for dual chamber sensing in the solo operating mode since FF R-waves may be sensed by the pacemaker even though the atrial pacemaker does not receive EGM signals from electrodes positioned in the ventricle. This "pseudo" dual chamber sensing of both NF P-waves and FF R-waves may not be used in the timing and control of atrial pacing pulses, however, and the solo pacing mode is therefore referred to as AAI(R).

The solo operating mode of the atrial pacemaker may additionally include FF ventricular pacing pulse monitoring (FF V PACE MONITORING ON). A FF sensing channel of the RA pacemaker may be enabled to sense FF ventricular pacing pulses to detect the presence of an intracardiac ventricular pacemaker.

At block 408, a ventricular pacemaker, such as RV pacemaker 14, may be detected. Detection of a ventricular pacemaker by the atrial pacemaker may be based on a received telemetry signal from an external device. Alternatively or additionally, the solo operating mode of the atrial pacemaker may include automatic detection of ventricular pacemaker based on FF ventricular pacing pulse monitoring enabled during the solo operating mode (block 404). If FF ventricular pacing pulses are sensed, detection of a ventricular pacemaker may be confirmed at block 408 based upon ventricular pacemaker detection criteria, e.g., a minimum required number of FF ventricular pacing pulse sensed events within a predetermined interval of time or predetermined number of atrial cardiac cycles (PP intervals). If no ventricular pacing pulses are sensed or the ventricular pacemaker detection criteria are not satisfied, and/or no notification signal is received from an external device, the atrial pacemaker remains in the solo mode (block 404).

A ventricular pacemaker, such as RV pacemaker 14 may be implanted, as indicated at block 420, at any time prior to, concomitantly with, or subsequently to the atrial pacemaker implantation. If RV pacemaker 14 is detected by RA pacemaker 12 at block 408, RA pacemaker 12 automatically configures itself in a duo operating mode at block 410. The atrial pacemaker duo operating mode may include adjustments to monitoring functions and/or therapy delivery functions.

For example, since a ventricular pacemaker is now present, AV block monitoring that was enabled during the solo operating mode for the purposes of determining a need for a ventricular pacemaker may be disabled or turned "off" at block 410. Since a ventricular pacemaker is available to provide back-up ventricular pacing, the atrial pacemaker may monitor for atrial tachycardia (AT) or atrial fibrillation (AF) according to an implemented tachyarrhythmia detection algorithm (AT/AF DETECTION ON). The atrial duo operating mode may enable atrial ATP therapy (ATRIAL ATP ON) in addition to providing bradycardia pacing. Without the ventricular pacemaker present, it may be undesirable to deliver atrial ATP since it could lead to an irregular ventricular rhythm. In response to detecting RV pacemaker 14, RA pacemaker 12 may automatically enable AT/AF detection and atrial ATP therapy capabilities.

During the duo operating mode, atrial bradycardia pacing may be configured to use a higher pacing pulse amplitude and/or pulse width than used during the solo mode for bradycardia pacing. For example, the atrial pacing pulse amplitude may be increased by increasing a pacing safety margin that is added to an atrial pacing capture threshold. A higher pacing safety margin may be used during the duo operating mode compared to the pacing safety margin used during the solo operating mode. The higher atrial pacing pulse amplitude resulting from adding a higher safety pacing margin promotes reliable sensing of the FF atrial pacing pulse by the ventricular pacemaker. Alternatively, a fixed high atrial pacing pulse amplitude or pulse width may be used during the duo operating mode that is expected to be above the atrial pacing capture threshold and easily sensed by the ventricular pacemaker as a FF pacing pulse with a high degree of confidence. As such, the self-configured duo operating mode may include increasing the pacing safety margin as indicated at block 410 or otherwise setting a high atrial pacing pulse amplitude or pulse width.

Upon configuring the duo operating mode at block 410, the atrial pacemaker provides a signal to the programmer or other external device, e.g., upon the next interrogation command from the external device, indicating the duo operating mode has been configured and enabling the external device to display relevant programmable control parameters. For example, even if AT/AF detection and atrial ATP are enabled, a user may still be able to turn these features on or off using the external programmer. When turned on, relevant programmable control parameters such as AT/AF detection criteria and ATP control parameters may be displayed.

Some parameters or features included in the duo operating mode may be non-programmable parameters. For example, the increased atrial pacing pulse amplitude may be a fixed parameter so that a user may not inadvertently set the amplitude too low to be reliably sensed by the ventricular pacemaker.

After switching to the duo operating mode, the atrial pacemaker may continue to monitor for the presence of the ventricular pacemaker. If the ventricular pacemaker is no longer present (or functioning), the atrial pacemaker may return to the solo mode by returning to block 404. Detecting that the ventricular pacemaker is no longer present may be based on receiving a notification from an external device or detecting a disappearance of FF ventricular pacing pulse sensed event signals from a FF sensing channel 224. An extended period time of no FF ventricular pacing pulse sensed event signals may be required to determine that the RV pacemaker 14 is no longer present compared to the time required to detect that RV pacemaker 14 is present based on sensing FF ventricular pacing pulses. For example, at least one day of no FF ventricular pacing pulse sensed events may be required before the RA pacemaker control module 206 determines that the RV pacemaker 14 is no longer present. The RV pacemaker 14 may be configured to deliver a predetermined number of pacing pulses, e.g., 8 pacing pulses, at an overdrive pacing rate greater than an intrinsic heart rate and/or at a high pulse output at least once per day to reduce the likelihood of RA pacemaker control module 206 determining that RV pacemaker 14 is no longer present. Similarly, RA pacemaker 12 may be configured to deliver a predetermined number of pacing pulses at an overdrive rate and/or increased pulse output to reduce the likelihood that RV pacemaker 14 does not falsely determine that RA pacemaker 12 is no longer present.

When a ventricular pacemaker, e.g., RV pacemaker 14 or an LV pacemaker, is implanted as indicated at block 420, it may initially determine if an atrial pacemaker is detected at block 422. Detection of an atrial pacemaker may be based on receipt of a telemetry notification signal from a programmer or other external device 20 or based on monitoring a ventricular EGM signal for the occurrence of FF atrial pacing pulses. The ventricular pacemaker may be provided in a solo mode as a default mode or a duo mode as a default mode. If the atrial pacemaker is detected at block 422, the ventricular pacemaker configures itself in the duo operating mode (which may be a matter of maintaining a default mode) at block 430. The duo operating mode of the ventricular pacemaker may alter both monitoring and therapy delivery functions of the ventricular pacemaker compared to the ventricular pacemaker solo operating mode.

For example, during the duo mode, the ventricular pacemaker may be configured to sense FF P-waves, which may include intrinsic or evoked P-waves, and FF atrial pacing pulses. The ventricular pacemaker may use the sensed atrial events, including both FF sensed atrial pacing pulses and FF sensed P-waves, for controlling the timing of the ventricular pacing pulses. As such, the ventricular duo operating mode configured at block 430 includes enabling FF atrial pacing pulse sensing.

The duo operating mode may include the options of VVI(R) and VDD(R) pacing modes. Alternatively, the duo operating mode may include only the VDD(R) pacing mode. During VVI(R) pacing, a NF R-wave sensed during an escape interval inhibits a scheduled ventricular pacing pulse and restarts the escape interval. FF atrial sensed events are not used to inhibit or trigger a ventricular pacing pulse. In the VDD(R) pacing mode, FF atrial sensed events, including FF atrial pacing pulse sensed events and FF P-wave sensed events, are used to trigger a ventricular pacing pulse at an AV interval to provide atrial-synchronized ventricular pacing. The synchronized single-chamber VDD(R) pacing mode of ventricular pacemaker in combination with the AAI(R) pacing mode of the atrial pacemaker provide DDD(R) pacing. By sensing FF atrial events by sensing module 204 in the ventricular pacemaker, the two separate atrial and ventricular intracardiac pacemakers, e.g. pacemakers 12 and 14, are enabled to provide DDD(R) pacing, which is described in greater detail below.

During the duo operating mode, the ventricular pacemaker pacing mode may be programmable as a VVI(R) mode or a VDD(R) mode. When programmed in a VVI(R) mode (instead of VDD(R) mode), with an atrial pacemaker present and operating in an AAI(R) mode, a DDI(R) mode is achieved (instead of a VDD(R) mode). The atrial pacemaker provides pacing and sensing in the atrial chamber and inhibits atrial pacing pulses in response to NF atrial sensed events. The ventricular pacemaker provides pacing and sensing in the ventricular chamber and inhibits ventricular pacing pulses in response to NF ventricular sensed events. The ventricular pacemaker is also enabled to sense FF atrial events but does not trigger a ventricular pacing pulse at an AV delay in response to a FF atrial sensed event as it does during a VDD(R) mode. A DDI(R) pacing mode is useful for patients with paroxysmal AF. An AV interval may be started in response to a FF atrial pacing pulse sensed event, but a FF non-paced sensed event, i.e., an intrinsic FF P-wave sensed event, does not start an AV interval. The ventricular pacemaker paces the ventricle at the programmed lower rate or the sensor indicated rate interval when FF P-wave sense events signals are produced (corresponding to intrinsic P-waves) in the absence of FF atrial pacing pulse sensed events.

Self-configuration of the duo operating mode by the ventricular pacemaker may further include enabling atrial tachycardia/atrial fibrillation (AT/AF) detection by the ventricular pacemaker and automatic pacing mode switching based on AT/AF detection, as indicated in block 430. The ventricular pacemaker may automatically switch between VDD(R) and VVI(R) pacing modes based on AT/AF detection by the ventricular pacemaker.

The atrial pacemaker may be enabled to detect the presence of AT/AF using NF P-wave sensing (as indicated at block 410) but may not be configured to send a communication signal to the ventricular pacemaker to indicate that an AT/AF detection has been made. The ventricular device may configured during the duo mode to detect AT/AF based on a disappearance of both FF atrial pacing pulse sensed events and FF P-wave sensed events. P-waves during AF will be relatively low amplitude compared to P-waves during sinus rhythm resulting in a loss of P-wave sensing or intermittent P-wave sensing. In some cases, FF P-wave sensed event signals could be produced at a high rate by the ventricular pacemaker sensing module during AF if the P-wave amplitude is high enough during AF. Accordingly, the ventricular pacemaker may be enabled to detect AF during a duo operating mode based on AF detection criteria which may include FF sensed event signals occurring below a minimum rate, no FF sensed event signals for a predetermined interval of time, and/or a FF P-wave sensed event signal rate that is greater than a predetermined pacing mode switch threshold rate.

Alternatively, the atrial pacemaker may be configured to detect AF and deliver atrial pacing pulses at a particular rate or sequence to signal the ventricular pacemaker that AF has been detected. The ventricular pacemaker detects AF in response to sensing the FF atrial pacing pulse events at the particular rate or sequence.

When AF is detected by the ventricular pacemaker, the control module 206 automatically switches the VDD(R) pacing mode to the VVI(R) pacing mode. A return of FF sensed event signals produced by the FF sensing channel 224 at a rate greater than a minimum rate and below a mode switch threshold rate causes the ventricular pacemaker control module 206 to return the pacing mode to VDD(R). In this way, the separate atrial pacemaker and ventricular pacemaker can operate cooperatively to provide dual chamber pacing in patients having AF by providing atrial-synchronized ventricular pacing, i.e., DDD(R) pacing, when AF is not detected by the ventricular pacemaker and DDI(R) pacing when AF is detected.

The ventricular duo operating mode may include other monitoring functions. For example, an AV conduction time (AVCT) test may be enabled at block 430. An AVCT test may be performed periodically to determine if AV conduction is intact in a patient that may have varying degrees of or intermittent AV block. The ventricular pacemaker control module 206 may periodically extend an AV interval being used to control the timing of ventricular pacing pulses following sensed FF atrial events to allow time for an intrinsic R-wave to be sensed. The time interval between a sensed FF atrial event, which may be a FF atrial pacing pulse sensed event or a FF P-wave sensed event, and a subsequently sensed NF R-wave is determined as the AV conduction time.

The duo operating mode configured at block 430 may further include enabling minimum ventricular pacing (MVP). The AVCT test enabled at block 430 may be used by the ventricular pacemaker control module 206 to control MVP according to when AVCT is within an acceptable range. If AVCT is within an acceptable normal range, the ventricular pacemaker switches to atrial-based pacing in which ventricular pacing is withheld and only back-up ventricular pacing pulses are delivered at a relatively long AV interval, which may be a long paced AV (P-AV) interval following an atrial pacing pulse sensed as a far field pacing pulse event or a long sensed AV (S-AV) interval following a far field P-wave sensed event. For example, the ventricular pacing mode may be a VDD(R) mode with a longer AV interval than when AVCT is not within a predetermined acceptable range. The atrial-based pacing minimizes the number of ventricular pacing pulses being delivered and promotes ventricular depolarization by the natural conduction system of the heart via the AV node. If one or more back-up ventricular pacing pulses are delivered, or if the AVCT is determined to be longer than an acceptable normal range during atrial-based pacing, the ventricular pacemaker control module switches to atrial-synchronized ventricular pacing at a desired AV interval following sensed FF atrial events (FF atrial pacing pulse sensed events or FF P-wave sensed events). Sensing of FF atrial events by the ventricular pacemaker in the duo operating mode is described in greater detail below.

Periodically, the ventricular pacemaker may extend the AV interval during atrial-synchronized ventricular pacing according to the AVCT test protocol to detect a return of AV conduction within a normal range. The ventricular pacemaker may switch back to atrial-based pacing in response to the return of AVCT to a normal range. While the AVCT test and MVP features may be enabled during the duo operating mode of the ventricular pacemaker, each feature may be programmably turned on or off by a user according to individual patient need. Other relevant operating parameters may be made accessible to a user on the programmer or other external device, for example for programming a desired AV interval during atrial-triggered ventricular pacing for optimized atrioventricular synchrony and a relatively longer AV interval for delivering back-up ventricular pacing pulses during atrial-based MVP.

In the duo operating mode, the combination of the atrial pacemaker and the ventricular pacemaker operate together in a DDD(R) or DDI(R) mode even though neither device is delivering pacing pulses to both the atrial and ventricular chambers and neither device is sensing NF signals in both the atrial and ventricular chambers. The atrial pacemaker is operating in an AAI(R) pacing mode and the ventricular pacemaker is operating in a VDD(R) pacing mode or a VVI(R) pacing mode with the added functionality of sensing FF atrial events to provide the pseudo dual chamber sensing and desired response to FF sensed events (atrial paced sensed events or P-wave sensed events). Together the two devices operate in a DDD(R) or DDI(R) pacing mode and thus provide a wholly intracardiac DDD(R) or DDI(R) pacing system.

If the atrial pacemaker is not detected by the ventricular pacemaker at block 422, upon initial implant or at any later time during the duo operating mode, the ventricular pacemaker self-configures in a solo operating mode at block 424. For example, if the ventricular pacemaker no longer detects FF atrial pacing pulses for a predetermined interval of time or receives a wireless telemetry notification signal from an external device indicating the atrial pacemaker is not present (at block 422), the ventricular pacemaker self-configures the solo operating mode at block 424.

In the solo mode configured at block 424, the sensing module 204 of the ventricular pacemaker may be enabled to sense ventricular R-waves only with VVI(R) being the only pacing mode available. Alternatively, the sensing module may be enabled to sense ventricular R-waves and FF P-waves with both VVI(R) and VDD(R) pacing modes available.

In the solo operating mode, therefore, both atrial-asynchronous ventricular pacing and atrial-synchronous ventricular pacing using FF P-wave sensing may be available. As indicated above, single chamber ventricular pacing with pseudo dual chamber sensing based on FF P-wave sensing is referred to herein as VDD(R) since pacing pulses are delivered in the ventricle, near-field R-waves and far-field P-waves are sensed in the ventricular and atrial chambers, respectively, using a single bipole of the single chamber device, and a dual response to sensed events is provided. The ventricular pacing pulse is inhibited in response to a NF R-wave sensed event signal during an AV interval, and a ventricular pacing pulse is triggered in response to a FF P-wave sensed event signal. In the solo operating mode, therefore, two different pacing modes may be selectable using external device 20. For example, a clinician or other user may be able to program the RV pacemaker 14 in FIG. 1 to a VVI(R) mode or VDD(R). Both options may be made available with corresponding programmable therapy control parameter settings, such as a lower rate for controlling ventricular pacing rate during the VVI(R) pacing mode and the AV interval for controlling the atrial-synchronized pacing pulses during VDD(R) pacing mode.

If the atrial pacemaker is detected during the solo mode at block 422, the ventricular pacemaker switches to the duo mode at block 430. The ventricular pacemaker may detect the presence of the atrial pacemaker in response to a wireless telemetry signal from an external device 20. Alternatively, the ventricular pacemaker solo operating mode may include monitoring FF atrial events periodically or continuously to detect FF atrial pacing pulses and thereby detect the presence of the atrial pacemaker.

An intracardiac pacemaker, atrial or ventricular, operating in a solo or duo mode may be configured to periodically deliver pacing pulses at an increased pacing pulse output, e.g., increased pulse amplitude and/or rate, to facilitate automatic detection of the pacemaker by another intracardiac pacemaker. For example, the atrial pacemaker self-configured in a solo operating mode at block 404 may periodically increase the atrial pacing pulse amplitude and/or periodically overdrive pace the atria if no atrial pacing pulses have been delivered for a predetermined interval of time. If no FF atrial pacing pulses are sensed by the ventricular pacemaker for an extended period of time due to sustained atrial sensing inhibiting the atrial pacing pulses, the ventricular pacemaker may incorrectly detect the removal or absence of the atrial pacemaker. Similarly, if no FF ventricular pacing pulses are sensed by the atrial pacemaker for an extended period of time due to ventricular sensed events inhibiting ventricular pacing pulses, the atrial pacemaker may incorrectly detect the removal or absence of the ventricular pacemaker.

As such, each pacemaker may be configured to periodically deliver pacing pulses at a rate that is greater than the intrinsic events, by shortening an appropriate pacing timing interval based on an atrial lower rate or SIR, ventricular lower rate or SIR, or AV interval. Periodic pacing at an interval shorter than intrinsic cardiac event intervals promotes FF sensing of pacing pulses by another pacemaker and thereby maintains detection of the presence of one pacemaker by the other pacemaker. In other examples, pacing pulses may be delivered in a particular sequence by varying the pacing intervals in a particular way so that the FF pacing pulse sensed event signals produced by FF sensing channel 224 can be easily identified by the control module 206 as evidence of the presence of the other pacemaker.

In various embodiments, the pacing pulses sensed as FF pacing pulse events by the first pacemaker are therapeutic pacing pulses delivered in another heart chamber by another intracardiac pacemaker. The therapeutic pacing pulses are sensed by the first pacemaker as FF pacing pulse events for detecting the presence of the other pacemaker as opposed to non-therapeutic communication signals transmitted by the other pacemaker to the first pacemaker.

Figure 6:
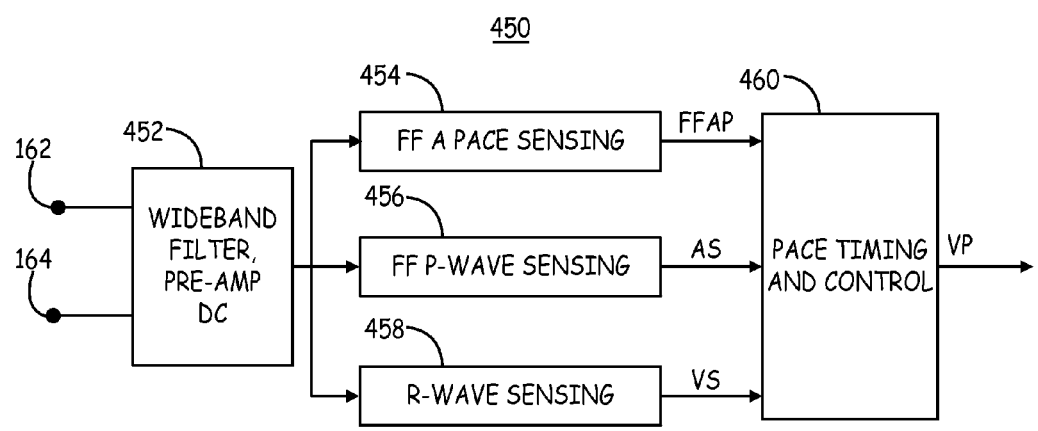
FIG. 6 is a functional block diagram of sensing and pacing control modules included in an intracardiac pacemaker according to one example.

FIG. 6 is a functional block diagram 450 of sensing and pacing control modules included in intracardiac pacemaker 100 according to one example. In this illustrative embodiment, the functionality represented by diagram 450 is described with reference to a ventricular intracardiac pacemaker such as RV pacemaker 14 configured to sense FF atrial pacing pulses, FF atrial P-waves associated with intrinsic or evoked depolarizations of the atria, and NF R-waves. It is recognized that the functionality can be adapted to be included in an atrial intracardiac pacemaker for sensing FF ventricular pace signals, FF R-waves and NF P-waves.

A single bipolar pair of electrodes 162 and 164 is used for sensing the FF and NF events and for delivering ventricular pacing pulses in this example. As described above in conjunction with FIGS. 2B and 2C, the inter-electrode spacing may be increased by an extender to improve sensing of FF signals. The EGM signal developed across electrodes 162 and 164 is received by a wide-band analog filter, pre-amplifier and digital converter (DC) circuit 452. The digital output of circuit 452 is provided to three sensing channels 454, 456 and 458.

Each of the sensing channels 454, 456 and 458 may include different digital filters and cardiac event detectors to enhance sensing different events by each channel based on amplitude threshold crossings. For example, FF P-wave sensing channel 456 may be provided with a different bandpass filter and sensing threshold than R-wave sensing channel 458 to promote reliable sensing of FF P-waves and NF R-waves by the respective sensing channels 456 and 458. In other examples, FF-P-wave sensing channel 456 and/or NF sensing channel 458 may be configured to sense FF P-waves and NF R-waves using other criteria than a sensing threshold crossing, such as waveform morphology criteria. Upon a P-wave sensing threshold crossing (or other sensing threshold criteria being met), FF P-wave sensing channel 456 produces an atrial sense (AS) signal (also referred to herein as a FF P-wave sensed event signal) that is passed to the pace timing and control 460.

The R-wave sensing channel 458 produces a ventricular sense (VS) signal (also referred to herein as a NF R-wave sensed event signal) that is passed to pace timing and control 460 in response to the EGM signal received from circuit 452 crossing an R-wave sensing threshold. If the current pacing mode is VVI(R), the VS signal will inhibit a ventricular pacing pulse and restart a pacing escape interval. Pace timing and control 460 will start a lower rate or SIR pacing escape interval in response to the VS signal and produce a VP signal if the escape interval expires before another VS signal is received. The VP signal is passed to the pulse generator 202 (not shown in FIG. 6) to cause delivery of a ventricular pacing pulse. If the current pacing mode is VDD(R), the VS signal will inhibit a ventricular pacing pulse and restart a lower rate or SIR pacing escape interval. If no AS signal is received from FF P-wave sensing channel 456 before expiration of the lower rate or SIR pacing escape interval, a ventricular pacing pulse is delivered. If an AS signal is received from FF P-wave sensing channel 456, pace timing and control 460 starts an AS-V interval to trigger ventricular pacing pulse delivery upon expiration of the AS-V interval. If a VS signal is received from R-wave sensing channel 458 during the AS-V interval, the pace timing and control inhibits the scheduled ventricular pacing pulse and restarts the lower rate or SIR escape interval.

The FF Apace sensing channel 454 is configured to produce a FFAP sense signal (also referred to herein as a FF atrial pacing pulse sensed event signal) in response to sensing a FF atrial pacing pulse. The FF Apace sensing channel 454 may include a narrow bandpass filter for passing a frequency characteristic of the atrial pacing pulse artifact. FF Apace sensing channel 454 may be configured to sense the atrial pacing pulse based on frequency content, slew rate, amplitude, pacing pulse artifact morphology, an over-range signal from the pre-amplifier in circuit 452, saturation of the digital convertor in circuit 452, or any combination thereof. FF Apace sensing channel 454 may correspond to apparatus and methods for sensing a pacing pulse delivered in another heart chamber as generally disclosed in provisionally-filed U.S. Pat. Application No. 61/984,249, hereby incorporated herein by reference in its entirety.

As further described below in conjunction with FIGS. 7 and 8, the pace timing and control 460 included in the pacemaker control module 206 is configured to select between a sensed AV interval (SA-V interval) and a paced AV interval (PA-V interval) for providing atrial synchronized ventricular pacing in a VDD(R) pacing mode. The SA-V interval is started in response to receiving an AS signal from FF P-wave sensing channel 456. The PA-V interval is started in response to receiving a FFAP signal from FF Apace sensing channel 454.

When the ventricular pacemaker is operating in a VVI(R) pacing mode, the FF Apace sensing channel 454 and the FF P-wave sensing channel 456 may be disabled or any FFAP and AS signals may be ignored by pace timing and control 460. If the ventricular pacemaker is configured in the solo operating mode with a VDD(R) pacing mode selected, the FF P-wave sensing channel 456 may be enabled to provide atrial-synchronized ventricular pacing. The FF Apace sensing channel 454 may be disabled or ignored by pace timing and control 460 since no atrial pacemaker is present to produce atrial pacing pulses during the solo operating mode of the ventricular pacemaker. The FF Apace sensing channel 454 may be enabled, periodically or continuously during the solo operating mode, however, to provide FFAP signals to the control module 206 of the ventricular pacemaker for the purpose of monitoring for the presence of an atrial intracardiac pacemaker.

When the ventricular pacemaker is configured in the duo operating mode with VDD(R) pacing, both the FF Apace sensing channel 454 and the FF P-wave sensing channel 456 are enabled and FFAP signals and AS signals received by pace timing and control 460 are used for setting respective PA-V intervals and SA-V intervals. When the pace timing and control 460 receives a FFAP signal, a subsequent AS signal during the PA-V interval is ignored. The AS signal may be produced in response to sensing an evoked P-wave following the FFAP signal. A P-wave sensing blanking window may be applied to FF P-wave sensing channel 456 in some examples for preventing an evoked P-wave from causing an AV interval to be restarted (i.e., an SA-V interval to be started during a PA-V interval) before delivering a pacing pulse at the PA-V interval.

Depending on the orientation of the atrial pacemaker and the ventricular pacemaker relative to one another, the atrial pacing pulse may not always be sensed by the ventricular pacemaker. For example, it is expected that when a RA pacemaker is substantially orthogonal to the RV pacemaker, sensing of the FF atrial pacing pulses is minimized. The relative orientation of the RA and RV pacemakers may be unknown and may change over time, e.g., due to respiration, posture or other motion. As such, the RV pacemaker may sense the FF atrial pacing pulse at times and at other times may sense the FF evoked P-wave. When the FF atrial pacing pulse is not sensed, the evoked P-wave sensed by the FF P-wave sensing channel 456 will cause an SA-V interval to be started by pace timing and control 460. Since the evoked response P-wave occurs upon atrial depolarization, the SA-V interval provides the proper timing of the ventricular pacing pulse for desired AV synchrony whether the AS signal is produced in response to sensing an intrinsic or an evoked FF P-wave.

When the atrial pacing pulse is sensed earlier than the evoked depolarization of the atrium, however, using the SA-V interval would cause the ventricular pacing pulse to be delivered earlier than the desired AV interval. Early contraction of the ventricle may truncate ventricular filling. As such, the PA-V interval, set longer than the SA-V interval, is selected in response to the FFAP signal. Otherwise the SA-V interval is selected in response to either an intrinsic or evoked FF P-wave, which may not be distinguished from each other by FF P-wave sensing channel 456.

In another example, the FFAP signal from FF Apace sensing channel 454 may cause pace timing and control 460 to set a short blanking interval then sense the evoked P-wave by FF P-wave sensing channel and start the SA-V interval in response to the AS signal. The FFAP signal is not used to start an AV interval but is used to prevent the pace artifact from being detected as an evoked FF P-wave and to indicate when to start looking for the evoked FF P-wave signal.

Figure 7:
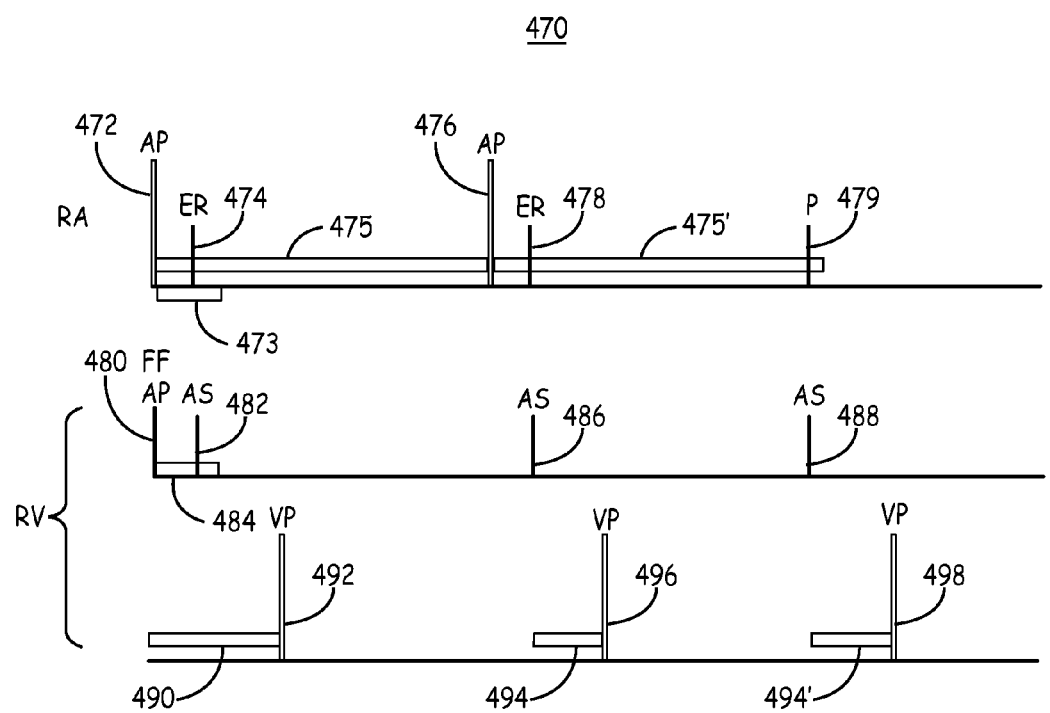
FIG. 7 is a timing diagram depicting the operation of right atrial and right ventricular intracardiac pacemakers when configured in duo operating modes.

FIG. 7 is a timing diagram 470 depicting the operation of RA pacemaker 12 and RV pacemaker 14 when configured in duo operating modes. The RA pacemaker 12 delivers an atrial pacing (AP) pulse 472, starts a lower rate (or SIR) escape interval 475, and delivers a next AP pulse 476 upon expiration of the escape interval 475. An atrial evoked response (ER) 474 caused by pacing pulse 472 may be ignored by the RA pacemaker by applying a blanking or refractory period 473 following AP 472 so that the escape interval 475 is not restarted in response to ER 474.

The RV pacemaker 14 senses the FF atrial pacing pulse and produces a FF atrial pacing pulse sensed event signal (FFAP) 480 that starts a PA-V interval 490. If an AS signal 482 is produced in response to sensing the ER 474 by the FF P-wave sensing channel (456 in FIG. 6), it does not cause an AS-V interval to be started during the PA-V interval 490. In some examples, a P-wave refractory period 484 may be applied following the FFAP signal 480 to ignore AS events that are likely to be evoked P-waves following the FFAP 480. If a NF R-wave is not sensed by the RV pacemaker during the PA-V interval 490, a ventricular pacing pulse (VP) 492 is delivered at the expiration of PA-V interval 490.

At expiration of the atrial escape interval 475, an AP 476 is delivered followed by an ER 478. In this case, the AP 476 is not sensed by the ventricular pacemaker, however the FF evoked P-wave corresponding to ER 478 is sensed as an AS event 486 by the FF P-wave sensing channel 456. An SA-V interval 494, that is shorter than PA-V interval 490, is started by the pace timing and control module (460 in FIG. 6) in response to the AS 486. Ventricular pacing pulse VP 496 is delivered upon expiration of the SA-V interval 494.

An intrinsic P-wave 479 occurs during the next atrial escape interval 475'. The P-wave 479 is sensed as a FF AS event 488 by the RV pacemaker 14. The RV pacemaker 14 starts the SA-V interval 494' and delivers a subsequent VP 498 at the same AV interval after intrinsic P-wave 479 as after the ER 478. By proper selection of a PA-V or SA-V interval by pace timing and control 460, each of VP 492, VP 496, and VP 498 are delivered at the same effective AV interval following atrial depolarization whether the depolarization is an evoked response 474 or 478 or an intrinsic P-wave 479 and regardless whether the atrial pacing pulse 472, 476 is sensed or not. The P-AV and the S-AV intervals may each take into account any delay in sensing the FF atrial events by the RV pacemaker 14.

Figure 8:
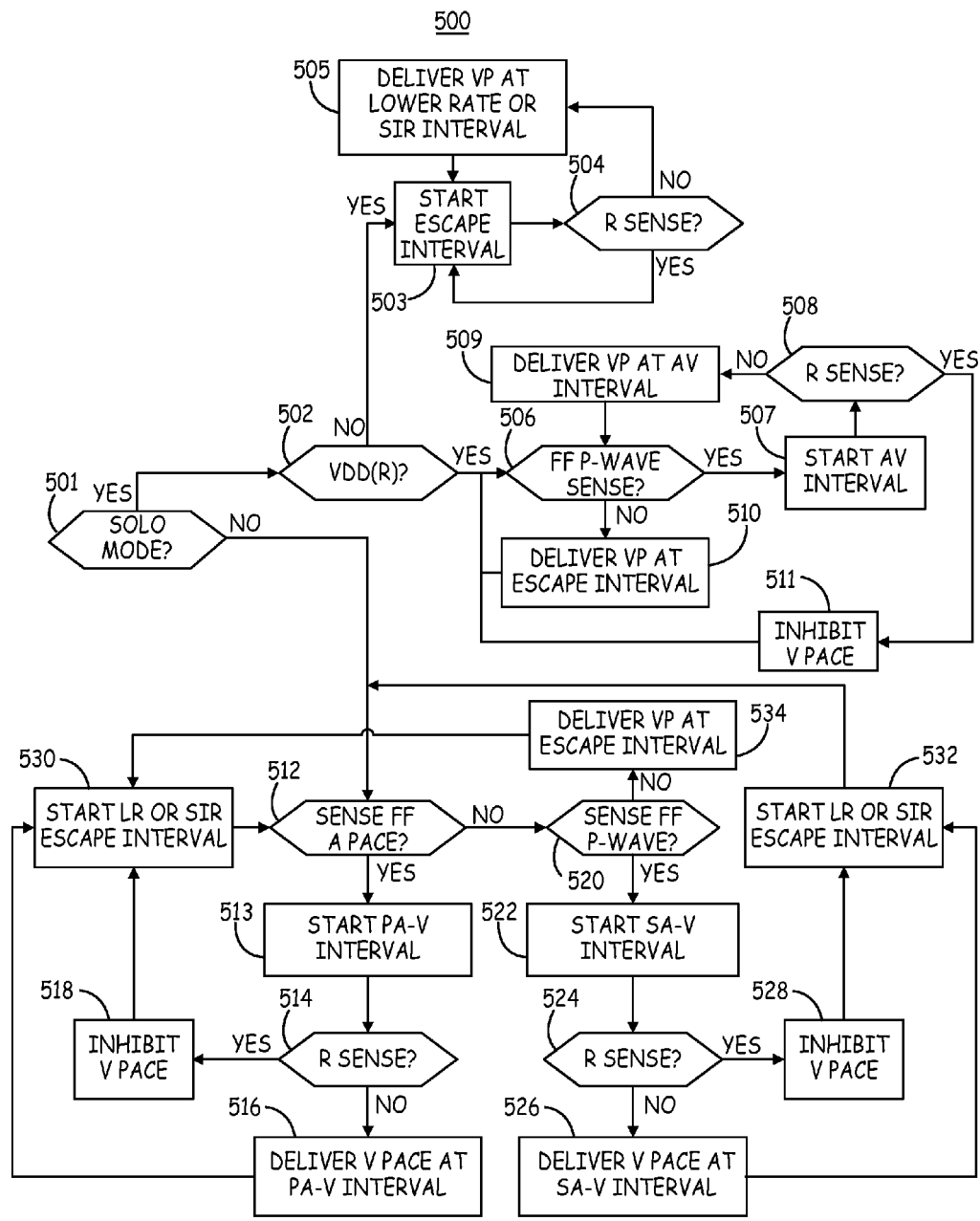
FIG. 8 is a flow chart of a method for controlling ventricular pacing by an intracardiac ventricular pacemaker.

FIG. 8 is a flow chart 500 of a method for controlling ventricular pacing by an intracardiac ventricular pacemaker, such as RV pacemaker 14 shown in FIG. 1. At block 501, the RV pacemaker 14 self-configures in either a solo or duo operating mode. Control module 206 self-configures the solo mode when no other implanted intracardiac pacemaker is present. The RV pacemaker 14 configures itself in a duo mode when an atrial intracardiac pacemaker, such as RA pacemaker 12, is present.

If the ventricular pacemaker operating mode is a solo mode ("yes" branch of block 501), the control module 206 may enable either a VVI(R) pacing (atrial asynchronous) or VDD(R) pacing (atrial synchronous) mode. A user may selectively program the pacing mode desired to be in effect during the solo operating mode. At block 502, the control module 206 determines if the currently programmed pacing mode is VVI(R) or VDD(R).

If the programmed pacing mode is VVI(R), the control module 206 starts a lower rate (or SIR) pacing escape interval to control a lower ventricular pacing rate at block 503. The escape interval is started in response to a delivered ventricular pacing pulse or in response to sensing a NF R-wave by the sensing module 204. If an R-wave is sensed at block 504 prior to the escape interval expiring, the escape interval is restarted at block 503. If an R-wave is not sensed prior to the escape interval expiring, a ventricular pacing pulse is delivered at block 505 at the expiration of the escape interval. The escape interval set at block 503 may be adjusted according to a sensor-indicated pacing rate to meet the metabolic needs of the patient, based for example on a patient activity signal received from an accelerometer.

The ventricular intracardiac pacemaker may remain in this VVI(R) pacing mode as long as the solo operating mode remains (as determined at block 501) and the programmed pacing mode remains VVI(R) (as determined at block 502).

The ventricular pacemaker may be programmed to operate in a VDD(R) pacing mode during the solo operating mode. The VDD(R) pacing mode includes delivering pacing pulses in the ventricle, pseudo dual chamber sensing by sensing both NF ventricular events and FF atrial events, and providing a dual pacing response to sensed events wherein pacing pulses are triggered by a FF atrial event and inhibited by sensing a NF ventricular event. The ventricular rate may be controlled in a rate-responsive manner based on a patient activity signal.

If the programmed pacing mode is VDD(R) during the solo operating mode (affirmative result at decision block 502), atrial-synchronized ventricular pacing is delivered. A patient may have normal sinus node function with AV conduction block requiring ventricular pacing. These patients may benefit from atrial-synchronized ventricular pacing requiring only an intracardiac ventricular pacemaker. When a FF P-wave is sensed at block 506, the control module 206 starts an AV interval at block 507.

If a NF R-wave is sensed at block 508, the ventricular pacing pulse scheduled to occur upon the expiration of the AV interval is inhibited at block 511 by starting a VV pacing escape interval set according to the lower rate (LR) or SIR. The control module 206 waits for the next FF P-wave sensed event at block 506. If no FF P-wave is sensed at block 506 before expiration of the VV pacing escape interval, a ventricular pacing pulse is delivered by pulse generator 202 at block 510.

If the AV interval started at block 507 in response to a sensed FF P-wave expires without sensing a NF R-wave at block 508, a ventricular pacing pulse (VP) is delivered at block 509 at the expiration of the AV interval. After delivering the VP, the control module 206 starts a VV pacing escape interval and waits for the next FF P-wave sensed event at block 506. All FF P-wave events sensed at block 506 are intrinsic P-waves since an atrial pacemaker is not present in this case. The VDDR pacing mode may be achieved by the intracardiac pacemaker positioned wholly in the ventricle and using a single bipolar pair of electrodes for delivering the ventricular pacing pulses, sensing the NF R-waves and the FF P-waves.

If the RV pacemaker 14 is operating in a duo operating mode (negative result at block 501), the RV pacemaker 14 monitors the EGM signal received by the sensing module 204 for a FF atrial pacing pulse event at block 512. For the sake of the flow chart 500, it is assumed that during the duo operating mode, the RV pacemaker 14 is programmed to deliver VDD(R) pacing, by default or by user selection. It is recognized, however, that depending on patient need, a VVI(R) pacing mode may still be available and programmed by a user during the duo operating mode, in which case the flow of blocks 503 through 505 would be followed.

In the duo operating mode with VDD(R) pacing mode programmed, if a FF atrial pacing pulse event is sensed at block 512, a PA-V interval is started at block 513. During the duo operating mode, the RV pacemaker control module 206 selects between an SA-V interval and an PA-V interval based on whether the FF sensing channel 224 has produced a FF atrial pacing pulse sensed event signal, as determined at block 512, or a FF P-wave sensed event signal as determined at block 520. The PA-V interval is started at block 513 in response to an affirmative result at decision block 512, and the SA-V interval is started at block 522 in response to an affirmative result at decision block 520. The PA-V interval is typically longer than the SA-V interval since there will be a short delay between delivery of the atrial pacing pulse and the evoked response of the atrium, though there may be cases that the PA-V is shorter than the SA-V depending on the relative conduction times of the atrial evoked response and the intrinsic atrial depolarization to the ventricle. If a NF R-wave is sensed during the PA-V interval at block 514, the ventricular pacing pulse is inhibited at block 518. The control module 206 restarts a LR or SIR escape interval at block 530 and waits for the next FF atrial sensed event at blocks 512 and 520, a FF atrial pacing pulse sensed event or a FF P-wave sensed event, whichever comes first. If the PA-V interval expires without sensing a NF R-wave at block 514, a ventricular pacing pulse is delivered at block 516 upon expiration of the PA-V interval.

If the next atrial sensed event is a FF P-wave, as determined at decision block 520, the control module 206 starts an SA-V interval at block 522. If a NF R-wave is not sensed prior to expiration of the SA-V interval (block 524), a ventricular pacing pulse is delivered by pulse generator 202 at block 526 upon expiration of the SA-V interval. If a NF R-wave is sensed during the SA-V interval (block 524), the ventricular pacing pulse is inhibited at block 528. The control module restarts a LR or SIR escape interval at block 532 and waits for the next sensed atrial event at block 512 or block 520. In this way, the RV pacemaker 14 selects from a PA-V interval or an SA-V interval based on whether the FF sensed atrial event is a FF sensed atrial pacing pulse (block 512) or a FF sensed P-wave (block 520). The resulting ventricular pacing pulses are delivered at a desired AV interval following the atrial depolarization, whether it is an evoked response or an intrinsic depolarization.

If neither a FF atrial pacing pulse nor a FF P-wave is sensed at blocks 512 or 520 during a LR or SIR escape interval started at blocks 530 or 532, the ventricular pacemaker delivers the ventricular pacing pulse upon expiration of the escape interval at block 534. A new escape interval is started at block 530 in response to the ventricular pacing pulse, and the control module 206 waits for the next FF sensed event at blocks 512 and 520.

During the atrial-synchronized ventricular pacing delivered by RV pacemaker 14 in the duo operating mode, the RA pacemaker 12 may be operating as an AAI pacemaker for pacing in the RA, sensing RA EGM signals, and inhibiting a RA pacing pulse in response to sensing a P-wave prior to the expiration of an atrial pacing escape interval. The RA pacemaker 12 operating as an AAI(R) pacemaker and the RV pacemaker operating as a VDD(R) pacemaker achieves DDD(R) pacing therapy delivered to the patient. The VDD (R) pacing is responsive to dual chamber sensing even though no sensing electrodes positioned in the atria are coupled directly to the RV pacemaker. Dual chamber sensing is achieved by sensing FF atrial events from the ventricular EGM signal. The FF atrial events may include atrial pacing pulses delivered by the RA pacemaker and FF P-waves, intrinsic or evoked. Thus a dual response of atrial-triggered ventricular pacing with ventricular pacing pulses inhibited by NF R-waves is achieved. A synchronized single chamber pacing mode is therefore available in both solo and duo operating modes where the single chamber pacing, in this case ventricular pacing, is synchronized to FF sensed events, in this case FF atrial events for achieving atrial-synchronized ventricular pacing.

Figure 9:
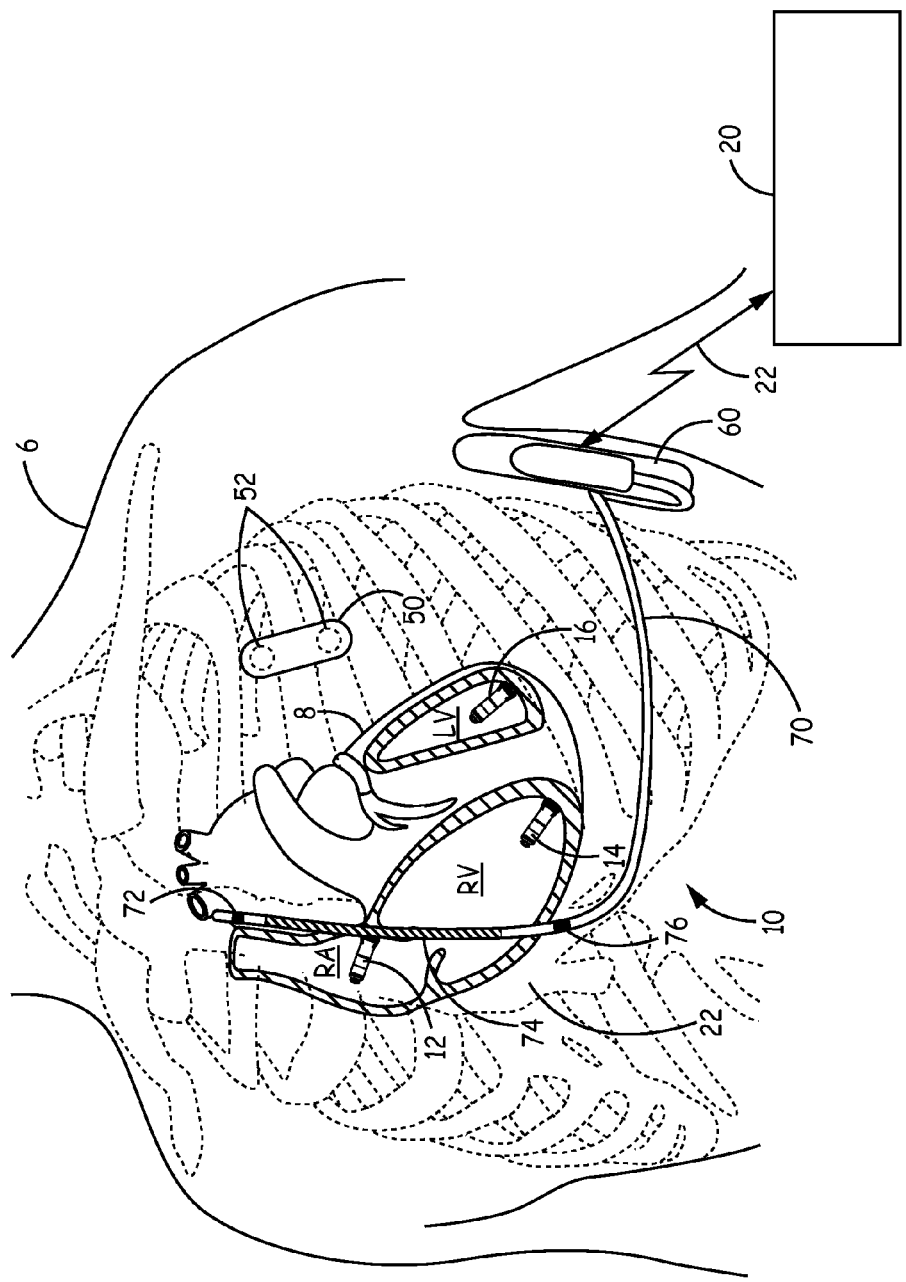
FIG. 9 is a conceptual diagram of another example of an IMD system including multiple, self-configuring intracardiac pacemakers and other extracardiac implantable medical devices.

FIG. 9 is a conceptual diagram of another example of an IMD system 10' including multiple, self-configuring intracardiac pacemakers and other implantable, extracardiac devices. IMD system 10' is shown to include RA pacemaker 12 and RV pacemaker 14 as previously shown in FIG. 1. Other IMDs that may be implanted in a patient include an LV intracardiac pacemaker 16 and extracardiac IMDs, such as ECG monitor 50 and ICD 60, which may be subcutaneously implanted devices. It is recognized that all of the IMDs 12, 14, 16, 50 and 60 may not be implanted in a single patient 6. Rather, the various intracardiac pacemakers 12, 14 and 16 and the extracardiac ECG monitor 50 and ICD 60 are shown to illustrate the various types of implantable devices that may be implanted to monitor a patient's heart 8 and/or deliver one or more therapies to heart 8.

ECG monitor 50 includes housing-based electrodes 52 for sensing a subcutaneous ECG signal for use in diagnosing a cardiac condition. ECG monitor 50 may correspond to the REVEAL® Insertable Loop Recorder, available from Medtronic, Inc., Minneapolis, Minn.

ICD 60 is shown coupled to a subcutaneous lead 70 which may carry sensing electrodes 72 and 76 for detecting tachyarrhythmias of heart 8 and a defibrillation electrode 74 for delivering high voltage cardioversion/defibrillation shock pulses to heart 8 in response to detecting tachycardia or fibrillation. ICD 60 and lead 70 may correspond to a subcutaneous ICD and lead system as generally disclosed in U.S. patent application Ser. No. 14/198,058 (Olson), hereby incorporated herein by reference in its entirety, or the above-incorporated '785 patent (Crutchfield). In other examples, ICD 60 may be coupled to a substernal, transvenous or other lead and electrode configuration.

Each of pacemakers 12, 14 and 16 include a control module capable of self-configuring an operating mode, in a solo, duo or trio operating mode, to establish available pacing modes, monitoring functions and associated programmable parameters of the pacemaker 12, 14 or 16 in response to establishing the presence of other ones of pacemaker 12, 14 or 16 as generally described in conjunction with FIG. 4 above. In addition, the control modules of each of pacemakers 12, 14 and 16 may be configured to modify a currently configured solo, duo or trio operating mode in response to establishing the presence of another implantable medical device besides an intracardiac pacemaker.

For example, RA pacemaker 12 may be capable of configuring itself in a solo operating mode, a modified solo operating mode in the presence of ICD 60, and a modified solo operating mode in the presence of ECG monitor 50. RA pacemaker 12 may be further capable of self-configuring a duo operating mode when the presence of a ventricular intracardiac pacemaker (RV or LV pacemaker 14 or 16) is present, a modified duo mode when a ventricular pacemaker 14 or 16 is present and ICD 60 is present and a modified duo mode when ventricular pacemaker 14 or 16 is present and ECG monitor 50 is present, and so on.

With each IMD added to the system 10' implanted in patient 6, the RA pacemaker 12 may establish an existing solo, duo or trio operating mode based on whether another pacemaker 14 or 16 is present and modify the established solo, duo or trio mode based on the presence of another IMD 50 or 60. A currently configured operating mode is modified when an IMD other than an intracardiac pacemaker is implanted by enabling or disabling a feature, adjusting a therapy delivery or monitoring control parameter, or enabling programmability of a control parameter by a user interacting with an external device 20. The operating mode is modified to disable functions that may be redundant between an intracardiac pacemaker 12, 14 or 16 and an extracardiac IMD 50 or 60 to conserve battery energy in the intracardiac pacemaker. The operating mode may additionally or alternatively be modified to add features which take advantage of the presence of an extracardiac, e.g., a subcutaneously implanted, IMD.

For example, RA pacemaker 12 may enable AV block monitoring in a solo operating mode for detecting a need for RV pacemaker 14 due to development of AV conduction block. AV block monitoring by RA pacemaker 12 may be disabled in a modified solo operating mode when ECG monitor 50 is present. ECG monitor 50 may be capable of collecting the data needed for monitoring AV block for determining a need for an RV pacemaker 14. Disabling AV block monitoring in RA pacemaker 12 during the solo mode will conserve battery life of the RA pacemaker 12.

In another example, a ventricular intracardiac pacemaker 14 or 16 may self-configure a duo operating mode for delivering DDD(R) pacing in conjunction with RA pacemaker 12 as described above. In one example, if both RV pacemaker and LV pacemaker are present with RA pacemaker 12, RV pacemaker may be self-configured in a trio operating mode that includes only right ventricular back up pacing, e.g., in a VVI mode. LV pacemaker 16 may be self-configured in a trio operating mode that includes VVI (R) and VDD(R) programmable pacing modes to provide atrial-synchronized LV pacing, with the RV pacemaker providing only back up RV pacing.

If ICD 60 is present, the ventricular pacemaker 14 or 16 may modify its self-configured operating mode to add ventricular tachycardia (VT) detection and ventricular ATP therapy delivery. For example, VT detection and ventricular ATP therapy may be available in the solo, duo or trio mode with FF atrial event sensing enabled since it may be desirable to discriminate VT from supraventricular tachycardia (SVT) using FF atrial sensed events. Ventricular ATP may be undesirable without the capability of cardioversion or defibrillation shock therapy provided by ICD 60 since VT could accelerate or deteriorate into ventricular fibrillation (VF).

As such, a modified solo, duo or trio operating mode of RV pacemaker 14 or LV pacemaker 16 may add ventricular ATP or other therapies that the intracardiac pacemaker 14 or 16 is capable of delivering but is not normally enabled to do so when ICD 60 is not present due to patient safety or other concerns. Various examples of VT detection and ATP therapies that may be implemented in a ventricular intracardiac pacemaker 14 or 16 are generally disclosed in commonly-assigned U.S. Pat. No. 7,515,960 (Sharma), U.S. Pat. No. 7,149,577 (Sharma, et al.), U.S. Pat. No. 7,623,911 (Sarkar, et al.), U.S. Pat. No. 7,742,812 (Ghanem, et al.), and U.S. Pat. No. 8,401,629 (Stadler, et al.), all of which patents are hereby incorporated herein by reference in their entirety.

Any of the intracardiac pacemakers 12, 14 or 16 may establish the presence of an extracardiac IMD 50 or 60 in response to an RF telemetry notification signal received from external device 20. Alternatively, intracardiac pacemakers 12, 14 or 16 may be configured to receive a communication signal from an extracardiac IMD 50 or 60 by an ultrasonic body bus communication signal as generally disclosed in U.S. Pat. No. 5,113,859 (Funke), hereby incorporated herein by reference in its entirety.

Thus, various examples of an implantable medical device system have been described according to illustrative embodiments. However, one of ordinary skill in the art will appreciate that various modifications may be made to the described embodiments without departing from the scope of the following claims.

The invention claimed is:

1. An implantable medical device system, comprising
a first implantable medical device that is configured to be implanted in a patient;
the first implantable medical device comprising a first control module configured to:
control operations of the first implantable medical device according to an operating mode of the first control module;
establish whether a second implantable medical device is functionally present or absent in the patient; and
self-configure the first control module between a first operating mode in response to establishing that the second implantable medical device is functionally present and a second operating mode in response to establishing that the second implantable medical device is functionally absent, wherein, according to configuration of the first control module, the second implantable medical device is functionally absent on condition that a battery of the second implantable medical device has reached a state where the second implantable medical device is non-functional in the implantable medical device system.

2. The system of claim 1, wherein the first implantable medical device comprises:
a first sensing module coupled to a pair of electrodes, the first sensing module comprising a near-field sensing channel configured to produce first sensed event signals in response to events occurring in a first heart chamber and a far-field sensing channel configured to produce second sensed event signals in response to events occurring in a second heart chamber;
the first control module configured to establish whether the second implantable medical device is present in response to the second sensed event signals received from the far-field sensing channel.

3. The system of claim 2, wherein the far-field sensing channel is configured to sense pacing pulses delivered by the second implantable medical device and produce far-field pacing pulse event signals, the first control module being enabled to establish that the second implantable medical device is present in the patient based on the second sensed event signals comprising sensed far-field pacing pulse event signals.

4. The system of claim 2, further comprising the second implantable medical device, wherein the second implantable medical device comprises:
   a second sensing module coupled to a pair of electrodes and comprising a near-field sensing channel producing first sensed event signals and a far-field sensing channel producing second sensed event signals;
   a pacing pulse generator coupled to the pair of electrodes;
   wherein the second implantable medical device is configured to self-configure by enabling selectable pacing modes comprising an asynchronous pacing mode and a synchronous pacing mode,
   the asynchronous pacing mode being selectably enabled for controlling pacing pulses to the second heart chamber based on the first sensed event signals received from the near-field sensing channel of the second sensing module but not based on the second sensed event signals received from the far-field sensing channel of the second sensing module,
   the synchronous pacing mode being selectably enabled for controlling pacing pulses delivered to the second heart chamber in response to the second sensed event signals received from the far-field sensing channel of the second sensing module and the first sensed event signals received from the near-field sensing channel of the second sensing module.

5. The system of claim 1, wherein the first implantable medical device comprises a pulse generator coupled to a pair of electrodes;
   wherein self-configuring the first operating mode by the first control module comprises selecting a first setting of a pacing pulse output parameter for controlling pacing pulses delivered by the pulse generator via the pair of electrodes,
   wherein self-configuring the second operating mode by the first control module comprises selecting a second setting of the pacing pulse output parameter that is used at least periodically for controlling pacing pulses delivered by the pulse generator, the second setting being different than the first setting.

6. The system of claim 1, wherein the first implantable medical device comprises:
   a sensing module coupled to a pair of electrodes, the sensing module comprising a near-field sensing channel producing first sensed event signals and a far-field sensing channel producing second sensed event signals;
   wherein the first control module is configured to determine a need for the second implantable medical device in response to the second sensed event signals when the first control module is self-configured in the first operating mode.

7. The system of claim 1, wherein the first control module is further configured to self-configure the second operating mode by enabling tachyarrhythmia detection and a tachyarrhythmia therapy.

8. The system of claim 1, further comprising an extracardiac implantable medical device, wherein the first control module is configured to:
   establish whether the extracardiac implantable medical device is present in the patient; and
   modify operating mode in response to the extracardiac implantable medical device being present.

9. The system of claim 8, wherein the first control module is configured to modify at least one of a therapy delivery control parameter or a monitoring control parameter in response to establishing the presence of the extracardiac implantable medical device.

10. The system of claim 1, wherein the second implantable medical device is functionally absent on condition that the second implantable medical device is implanted but incapable of operating together with the first implantable medical device in the implantable medical device system.

11. The system of claim 1, wherein the second implantable medical device is functionally absent on condition that the second implantable medical device is disabled.

12. The system of claim 1, wherein the second implantable medical device is functionally absent on condition that the second implantable medical device is incapable of therapy delivery.

13. The system of claim 1, wherein the second implantable medical device is functionally absent on condition that the battery of the second implantable medical device has reached end-of-life.

14. A method performed by an implantable medical device system, comprising:
   establishing by a first control module of a first implantable medical device, that is configured to be implanted in a patient, whether a second implantable medical device is functionally present or absent in the patient; and
   self-configuring the first control module between a first operating mode in response to establishing that the second implantable medical device is functionally present and a second operating mode in response to establishing that the second implantable medical device is functionally absent, wherein, according to configuration of the first control module, the second implantable medical device is functionally absent on condition that a battery of the second implantable medical device has reached a state where the second implantable medical device is non-functional in the implantable medical device system.

15. The method of claim 14, further comprising:
   producing first sensed event signals by a near-field sensing channel of a sensing module of the first implantable medical device in response to events occurring in a first heart chamber;
   producing second sensed event signals by a far-field sensing channel of the sensing module in response to events occurring in a second heart chamber; and
   establishing whether the second implantable medical device is present in response to the second sensed event signals.

16. The method of claim 15, further comprising:
   sensing pacing pulses by the far-field sensing channel that are delivered by the second implantable medical device;
   producing sensed far-field pacing pulse event signals in response to sensing the pacing pulses; and
   establishing that the second implantable medical device is present in the patient based on the second sensed event signals comprising the sensed far-field pacing pulse event signals.

17. The method of claim 14, wherein:
   self-configuring the first operating mode by the first control module comprises selecting a first setting of a pacing pulse output parameter for controlling pacing pulses delivered by the first implantable medical device; and self-configuring the second operating mode by the first control module comprises selecting a second setting of the pacing pulse output parameter that is used at least periodically for controlling pacing pulses delivered by the first implantable medical device, the second setting different than the first setting.

18. The method of claim 17, further comprising:
producing first sensed event signals by a near-field sensing channel of a sensing module of the first implantable medical device;
producing second sensed event signals by a far-field sensing channel of the sensing module of the first implantable medical device; and
determining a need for the second implantable medical device in response to the second sensed event signals when the first control module is self-configured in the first operating mode.

19. The method of claim 15, further comprising:
producing first sensed event signals by a near-field sensing channel of a sensing module of the second implantable medical device;
producing second sensed event signals by a far-field sensing channel of the sensing module of the second implantable medical device;
self-configuring a control module of the second implantable medical device by enabling selectable pacing modes comprising an asynchronous pacing mode and a synchronous pacing mode,
the asynchronous pacing mode selectably enabled for controlling pacing pulses to the second heart chamber based on the first sensed event signals received from the near-field sensing channel of the second implantable medical device but not based on the second sensed event signals received from the far-field sensing channel of the second implantable medical device,
the synchronous pacing mode selectably enabled for controlling pacing pulses delivered to the second heart chamber in response to the second sensed event signals received from the far-field sensing channel of the second implantable medical device and the first sensed event signals received from the near-field sensing channel of the second implantable medical device.

20. The method of claim 14, further comprising self-configuring the second operating mode by enabling tachyarrhythmia detection and a tachyarrhythmia therapy.

21. The method of claim 14, further comprising:
establishing by the first control module whether an extracardiac implantable medical device is present in the patient; and
modifying operating mode of the first control module in response to the extracardiac implantable medical device being present.

22. The method of claim 21, further comprising modifying at least one of a therapy delivery control parameter or a monitoring control parameter in response to establishing the presence of the extracardiac implantable medical device.

23. A non-transitory, computer-readable storage medium storing a set of instructions that when executed by a control module of a first implantable medical device, that is configured to be implanted in a patient, included in an implantable medical device system cause the system to:
establish whether a second implantable medical device is functionally present or absent in the patient; and
self-configure the control module between a first operating mode in response to establishing that the second implantable medical device is present and a second operating mode in response to establishing that the second implantable medical device is functionally absent, wherein, according to configuration of the control module, the second implantable medical device is functionally absent on condition that a battery of the second implantable medical device has reached a state where the second implantable medical device is non-functional in the implantable medical device system.

\* \* \* \* \*